United States Patent
Butler et al.

(10) Patent No.: US 8,512,407 B2
(45) Date of Patent: Aug. 20, 2013

(54) EXPANDABLE SPINAL INTERBODY AND INTRAVERTEBRAL BODY DEVICES

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 604 days.

(21) Appl. No.: 12/789,257

(22) Filed: May 27, 2010

(65) Prior Publication Data

US 2010/0305705 A1 Dec. 2, 2010

Related U.S. Application Data

(62) Division of application No. 11/394,719, filed on Mar. 31, 2006, now Pat. No. 7,731,751.

(60) Provisional application No. 60/666,945, filed on Mar. 31, 2005.

(51) Int. Cl.
*A61F 2/44* (2006.01)

(52) U.S. Cl.
USPC ............. 623/17.16; 623/17.11; 606/279

(58) Field of Classification Search
USPC 606/246–249, 279; 623/17.11, 17.15–17.16, 623/23.47
See application file for complete search history.

(56) References Cited

U.S. PATENT DOCUMENTS

| | | | |
|---|---|---|---|
| 4,636,217 A | 1/1987 | Ogilvie et al. | |
| 5,390,683 A | 2/1995 | Pisharodi | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,126,689 A | 10/2000 | Brett | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |

(Continued)

FOREIGN PATENT DOCUMENTS

WO WO 2006/0105437 A2 10/2006

OTHER PUBLICATIONS

"Bacfuse® Spinous Process Fusion Plate Surgical Technique", © 2011, Pioneer Surgical, 12 pages.

(Continued)

*Primary Examiner* — Nicholas Woodall
*Assistant Examiner* — Larry E Waggle, Jr.
(74) *Attorney, Agent, or Firm* — Foley & Lardner LLP

(57) ABSTRACT

A device for insertion into a spinal (intervertebral or intravertebral) space is expandable from a first circumference to a second circumference through axial compression of segments of the device, particularly once the device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference.

18 Claims, 22 Drawing Sheets

(56) References Cited

U.S. PATENT DOCUMENTS

| | | |
|---|---|---|
| 6,235,030 B1 | 5/2001 | Zucherman et al. |
| 6,375,682 B1 | 4/2002 | Fleischmann et al. |
| 6,409,766 B1 | 6/2002 | Brett |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,648,917 B2 | 11/2003 | Gerbec et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,773,460 B2 | 8/2004 | Jackson |
| 6,796,983 B1 | 9/2004 | Zucherman et al. |
| 7,087,055 B2 | 8/2006 | Lim et al. |
| 7,101,375 B2 | 9/2006 | Zucherman et al. |
| 7,695,513 B2 | 4/2010 | Zucherman et al. |
| 2003/0236520 A1* | 12/2003 | Lim et al. ............ 606/61 |
| 2004/0153156 A1 | 8/2004 | Cohen et al. |
| 2004/0167625 A1 | 8/2004 | Beyar et al. |
| 2005/0033437 A1 | 2/2005 | Bao et al. |
| 2005/0131536 A1 | 6/2005 | Eisermann et al. |
| 2005/0143827 A1 | 6/2005 | Globerman et al. |
| 2005/0222681 A1* | 10/2005 | Richley et al. ........... 623/17.11 |
| 2005/0228391 A1 | 10/2005 | Levy et al. |
| 2005/0261769 A1* | 11/2005 | Moskowitz et al. ...... 623/17.11 |
| 2005/0278036 A1* | 12/2005 | Leonard et al. .......... 623/23.47 |
| 2006/0036258 A1 | 2/2006 | Zucherman et al. |
| 2006/0084988 A1* | 4/2006 | Kim ................................ 606/61 |
| 2006/0095136 A1 | 5/2006 | McLuen |
| 2006/0189999 A1 | 8/2006 | Zwirkoski |
| 2006/0264938 A1 | 11/2006 | Zucherman et al. |
| 2007/0142915 A1 | 6/2007 | Altarac et al. |
| 2008/0161818 A1 | 7/2008 | Kloss et al. |
| 2008/0177391 A1 | 7/2008 | Mitchell et al. |
| 2008/0312741 A1 | 12/2008 | Lee et al. |

OTHER PUBLICATIONS

International Search Report for Application No. PCT/US06/12060, date of mailing Apr. 5, 2007, 1 page.
Written Opinion of the International Searching Authority for Application No. PCT/US06/12060, date of mailing Apr. 5, 2007, 3 pages.
International Preliminary Report on Patentability for Application No. PCT/US06/12060, date of completion Jul. 18, 2007, 3 pages.

* cited by examiner

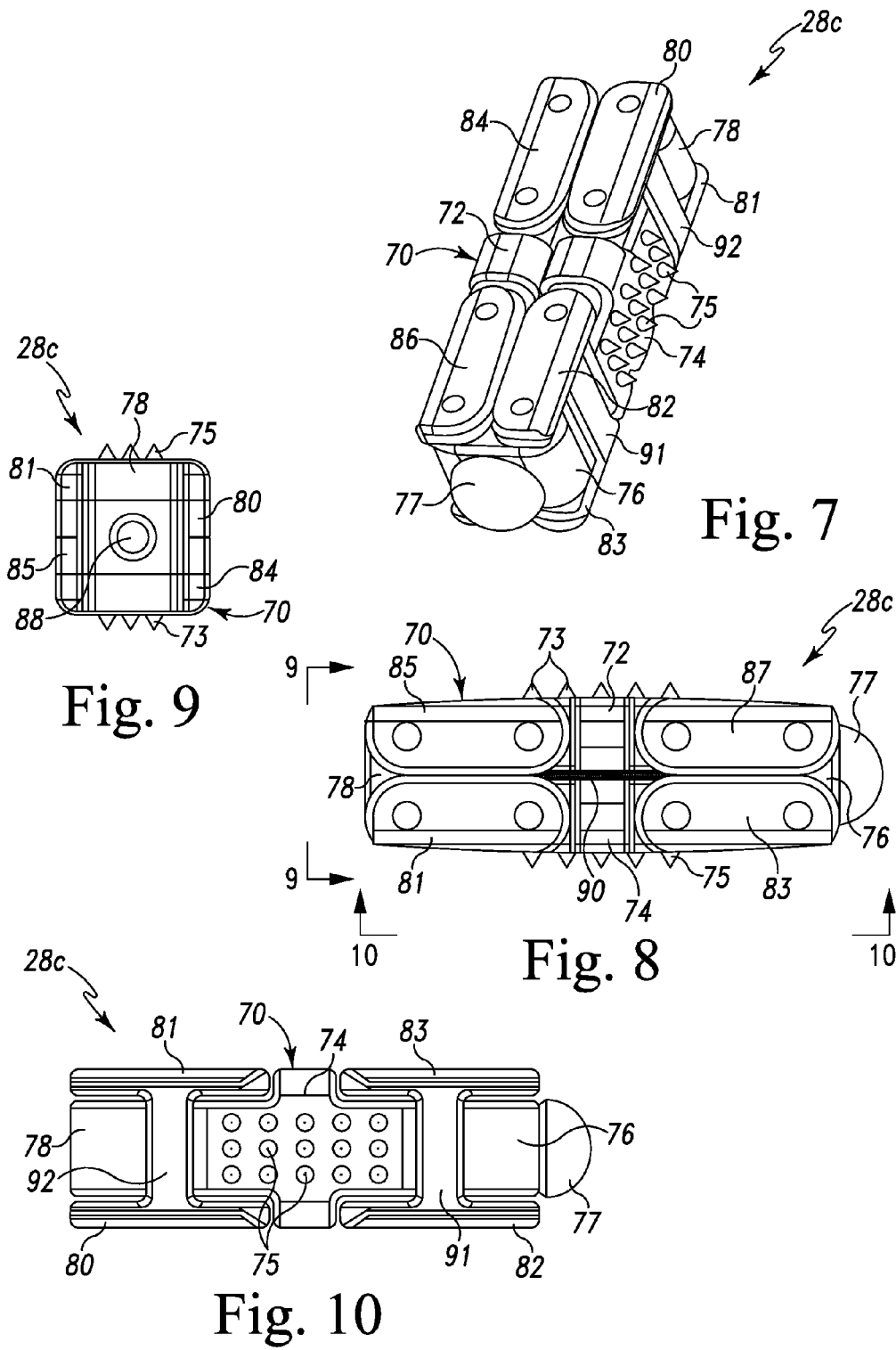

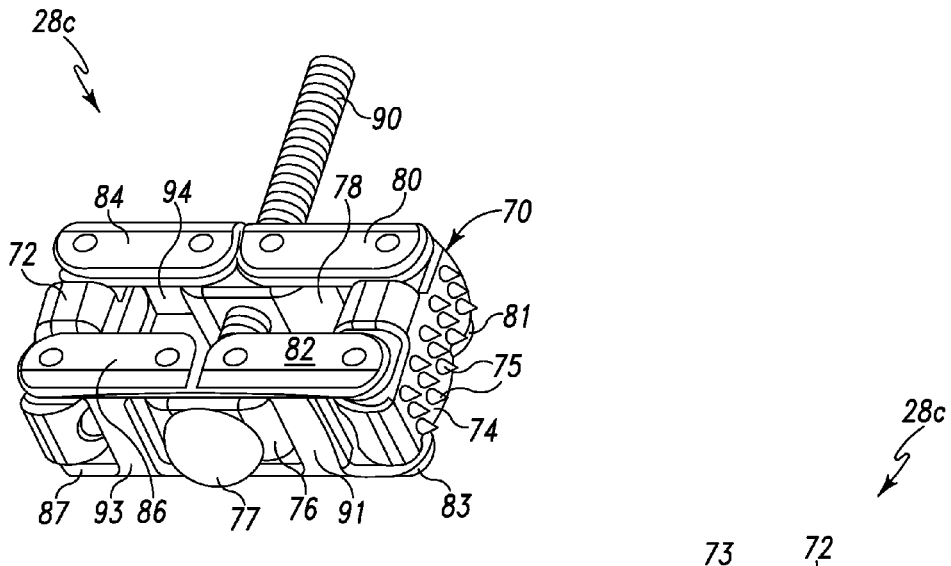
Fig. 11
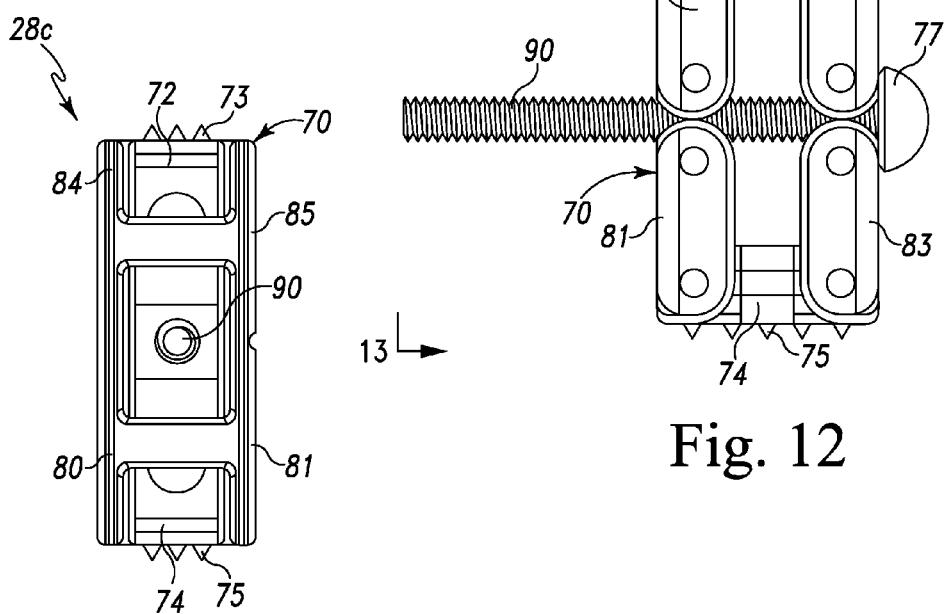
Fig. 13
Fig. 12

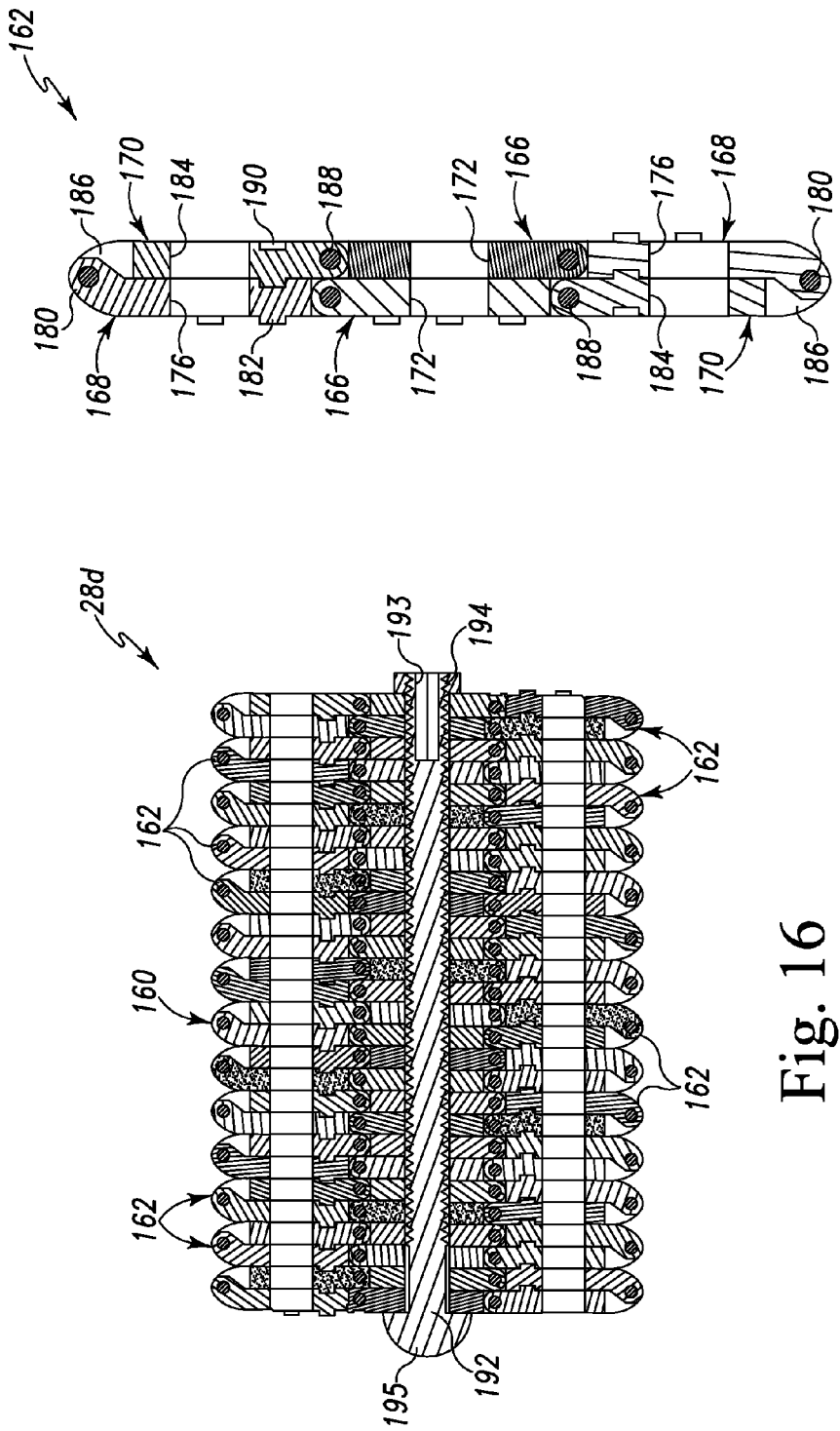

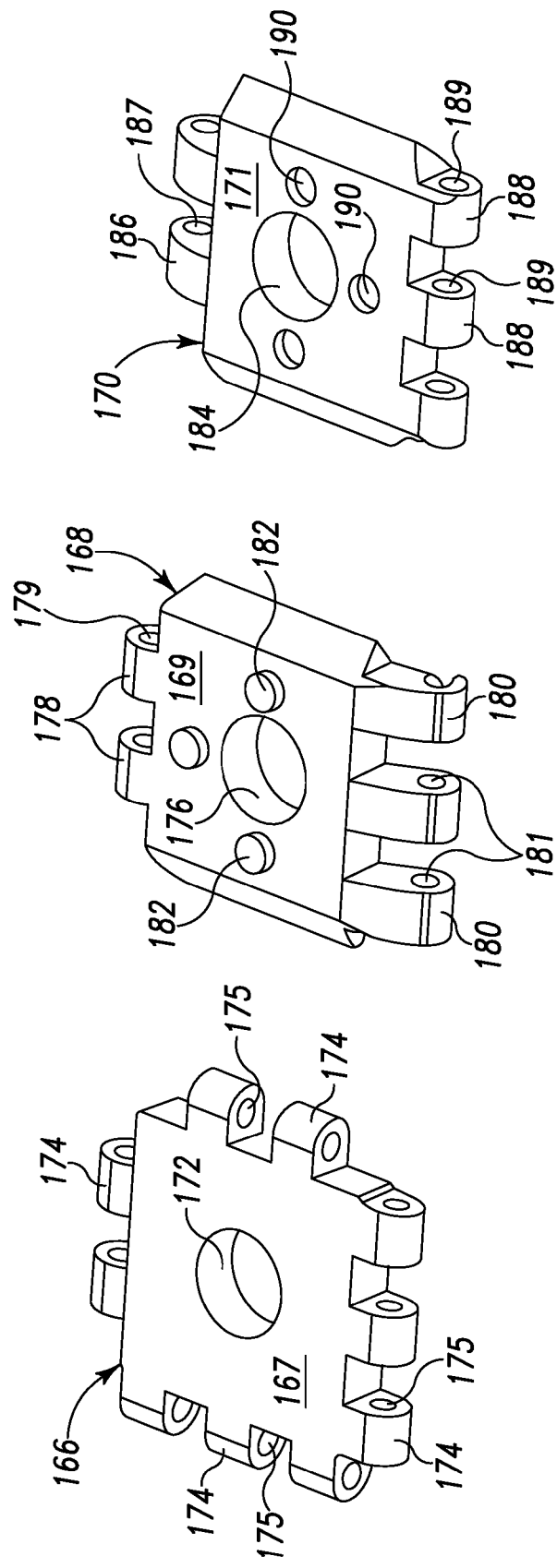

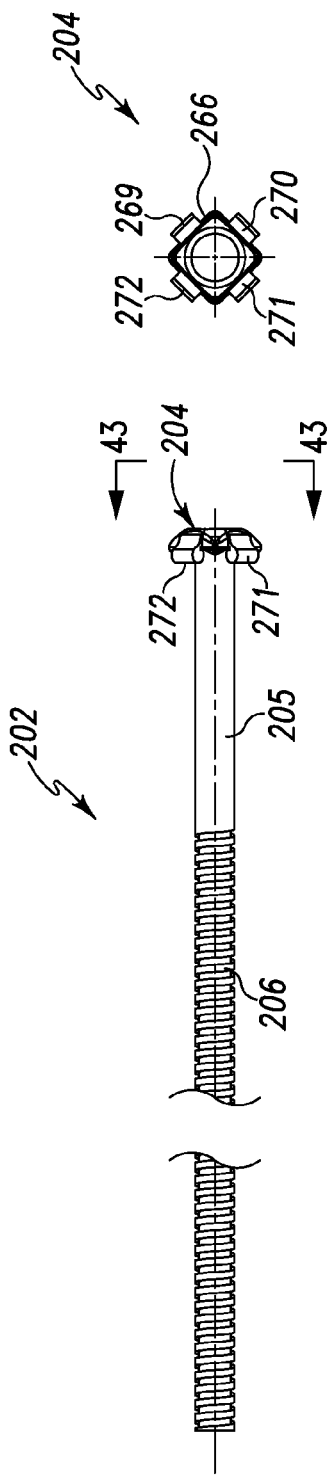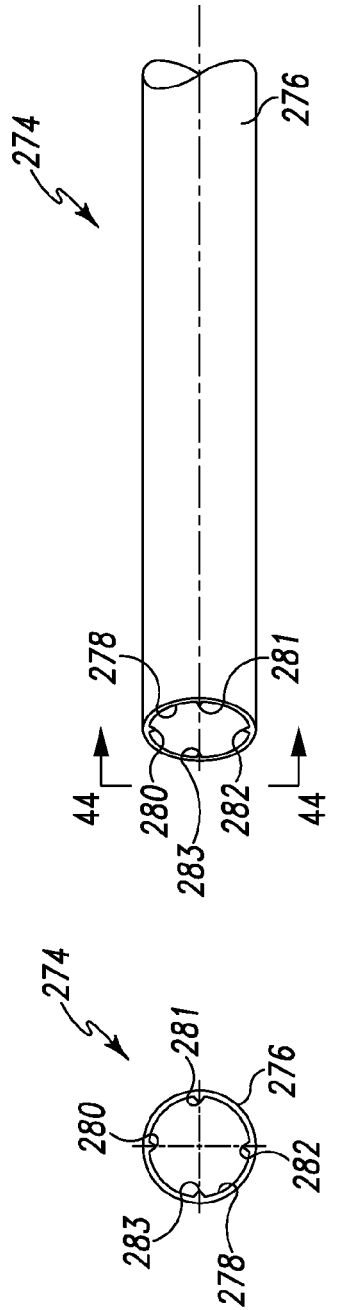

EXPANDABLE SPINAL INTERBODY AND INTRAVERTEBRAL BODY DEVICES

CROSS-REFERENCE TO RELATED APPLICATIONS

This patent application is a divisional application of U.S. application Ser. No. 11/394,719 filed on Mar. 31, 2006, entitled "Expandable Spinal Interbody and Intravertebral Body Devices," which claims the benefit of and/or priority to U.S. Application No. 60/666,945 filed Mar. 31, 2005, entitled "Dynamic Interbody Stabilization Devices," the entire contents of which are hereby specifically incorporated herein by reference.

FIELD OF THE INVENTION

The present invention relates to spinal interbody and intravertebral body devices and, more particularly, to vertebral interbody and intravertebral devices that are expandable after spinal placement thereof.

BACKGROUND OF THE INVENTION

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

However, current expandable spinal devices lack strength, reliability and/or simplicity of design.

In view of the above, it is desirable to provide expandable spinal devices that address prior art concerns.

In view of the above, it is desirable to provide expandable spinal interbody devices that address prior art concerns.

In view of the above, it is desirable to provide expandable spinal intravertebral body devices that address prior art concerns.

SUMMARY OF THE INVENTION

The present invention provides expandable spinal interbody and intravertebral body devices for insertion and maintenance between adjacent vertebrae and inside a vertebra of the spine. Particularly, the present invention provides various embodiments of expandable and/or dynamic vertebral interbody and intravertebral body devices that expand from a first radial profile into a second radial profile.

One or more of the present various expandable interbody and intravertebral devices may also provide a dynamization, mobilization or artificial disk platform. One or more of the various dynamic expandable interbody/intravertebral body devices as an artificial disk platform thus allows micro motion of the spine to occur. Additionally, one or more of the present various dynamic expandable interbody/intravertebral devices may function as a fusion device when bone, therapeutic agent or the like is included therein.

In one form, an expandable vertebral interbody/intravertebral body device for insertion into a vertebral space is provided. The interbody/intravertebral body device is expandable from a first circumference (radial profile) to a second circumference (radial profile) through axial compression of segments of the vertebral interbody/intravertebral body device, particularly once the interbody/intravertebral body device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference. The vertebral interbody/intravertebral body device may be formed of a bio-compatible radiolucent material. The radial profile of an interbody/intravertebral body device is easily defined by plate or leaf structures of the segments.

BRIEF DESCRIPTION OF THE DRAWINGS

The foregoing and other features of the present invention will become more apparent to one skilled in the art upon also reading the following description of embodiments with reference to the accompanying drawings wherein:

FIG. 7 is a perspective view of an exemplary embodiment of an expandable interbody/intravertebral body device in accordance with the present principles, the interbody/intravertebral body device shown in a pre-implant or unexpanded state;

FIG. 8 is a side view of the expandable interbody/intravertebral body device of FIG. 7;

FIG. 9 is a left side view of the expandable interbody/intravertebral body device of FIG. 8 taken along line 9-9 thereof;

FIG. 10 is a bottom view of the expandable interbody/intravertebral body device of FIG. 8 taken along line 10-10 thereof;

FIG. 11 is a perspective view of the expandable interbody/intravertebral body device of FIG. 7 shown in a post-implant or expanded state;

FIG. 12 is a side view of the expandable interbody/intravertebral body device of FIG. 11;

FIG. 13 is a right side view of the expandable interbody/intravertebral body device of FIG. 12 taken along line 13-13 thereof;

FIG. 16 is a sectional view of the expandable interbody/intravertebral body device of FIG. 15 taken along line 16-16 thereof;

FIG. 17 is an enlarged sectional view of a single segment, section or petal of the expandable interbody/intravertebral body device of FIG. 16, the single segment shown in an expanded position;

FIG. 20 is an enlarged perspective view of an end plate of the expandable interbody/intravertebral body segment of FIG. 18;

FIG. 21 is an enlarged perspective view of a first interconnect plate of the expandable interbody/intravertebral body segment of FIG. 18;

FIG. 22 is an enlarged perspective view of a second interconnect plate of the expandable interbody/intravertebral body segment of FIG. 18;

FIG. 42 is a side view of an implant and deploy rod for use with the expandable interbody/intravertebral body device of FIG. 23;

FIG. 43 is a right side (end) view of the rod of FIG. 42 taken along line 43-43 thereof;

FIG. 44 is an end view of an exemplary insertion and deployment cannula for the various expandable interbody/intravertebral body devices taken along line 44-44 of FIG. 45;

FIG. 45 is a side view of the exemplary insertion and deployment cannula of FIG. 44;

Figure 1:
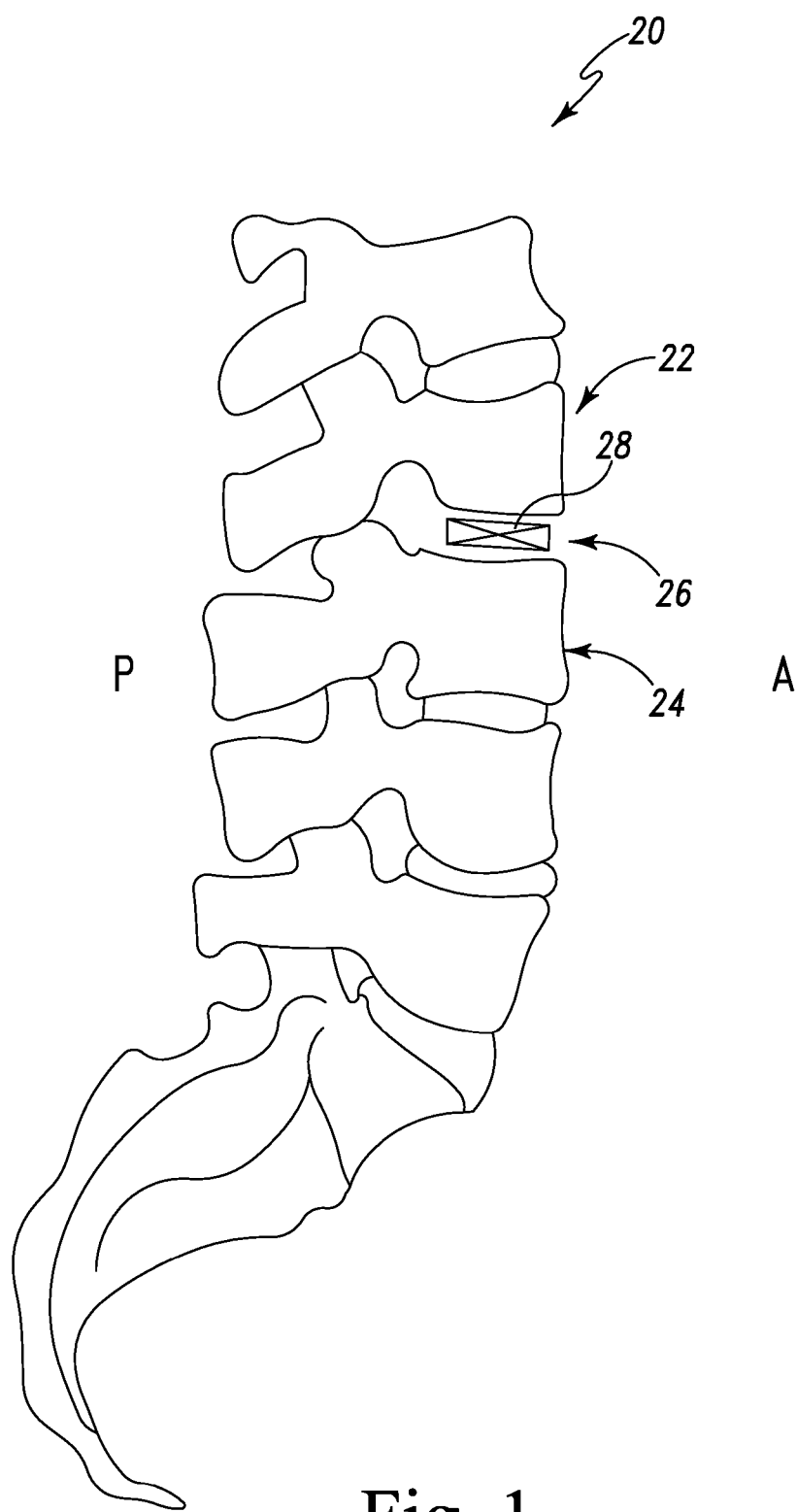
FIG. 1 is a side view of a portion of a human spine illustrating inter-vertebral placement of an expandable interbody/intravertebral body device in accordance with the principles of the present invention.

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION OF THE INVENTION

The present invention relates to expandable and/or dynamic interbody (between adjacent vertebrae), intravertebral body devices (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present invention provides various versions of dynamic (expandable and/or expandable and retractable) interbody/intravertebral body devices that are usable in a spinal column of a human. As representative of each one of the various versions of the present invention, FIG. 1 illustrates a representative dynamic spinal body device 28. The spinal body 28 is depicted as implanted or inserted into a human spine of which only a lower portion 20 of the spine is shown. The spinal device 28 is illustrated implanted between adjacent upper and lower vertebrae 22, 24 of the spine portion 20 in FIG. 1 (hence interbody or intervertebral). A spinal device 28 illustrated as body 28f is shown as implanted into a vertebra (hence intravertebral body) in FIGS. 57 and 58. Vertebrae 22 and 24 have portions that face anteriorly ("A", and from the right as viewed in FIG. 1) and portions that face posteriorly ("P", and from the left as viewed in FIG. 1).

Figure 2:
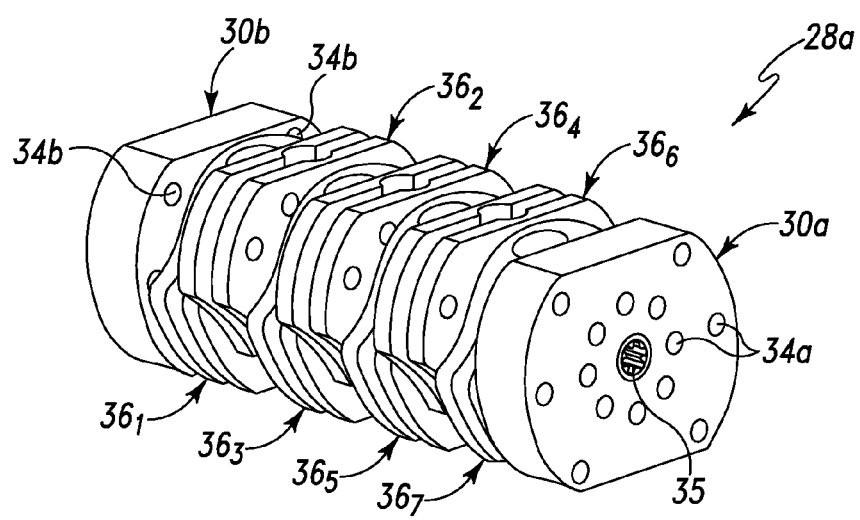
FIG. 2 is a perspective view of an exemplary embodiment of an expandable interbody/intravertebral body device in accordance with the present principles, the expandable interbody/intravertebral body device depicted in a pre-implant or unexpanded state.
Figure 3:
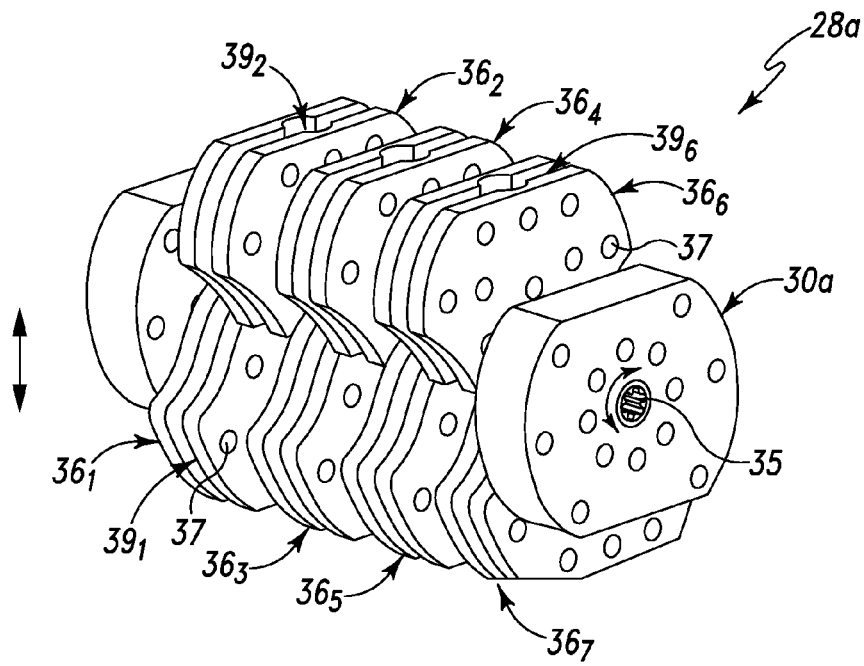
FIG. 3 is a perspective view of the expandable interbody/intravertebral body device of FIG. 2 depicted in a post-implant or expanded state.

Referring to FIGS. 2 and 3, there is depicted an embodiment of an expandable and retractable interbody/intravertebral body device generally designated 28a. FIG. 2 depicts the interbody/intravertebral body device 28a in a fully unexpanded or fully retracted position, while FIG. 3 depicts the interbody/intravertebral body device 28a in a fully expanded or fully un-retracted position. Of course, the interbody/intravertebral body device 28a may be positioned anywhere between the fully expanded to fully retracted positions.

The interbody/intravertebral body device 28a is a posterior (can be inserted in any direction) inserted interbody/intravertebral body device that provides controlled, vertical expansion within the intervertebral space 26 as well as vertical retraction within the intervertebral space 26. The interbody/intravertebral body device 28a includes identical end plates 30a, 30b each having holes or bores 34a, 34b therethrough. A central axis or shaft 35 has ends retained in each end plate 30a, 30b for rotation of the shaft 35. The ends of the shaft 35 are configured to receive a tool for rotation of the shaft and the expansion or retraction of a plurality of plates $36_1$, $36_2$, $36_3$, $36_4$, $36_5$, $36_6$, and $36_7$.

Each one of the plurality of plates 36 includes holes or bores 37. Additionally, each plate 36 is partially bifurcated creating a slot 39 in each plate. The plates 36 are connected to the shaft 35 such that one set of plates $36_1$, $36_3$, $36_5$, and $36_7$ move in one outward direction (expansion) upon shaft rotation in a first direction while another set of plates $36_2$, $36_4$, and $36_6$ move in another (opposite) outward direction (expansion) upon shaft rotation in the first direction. Shaft rotation in a second direction causes both sets of plates to retract. The adjustment of the expansion/retraction of the plates $36_1$, $36_2$, $36_3$, $36_4$, $36_5$, $36_6$, and $36_7$ is done in situ. The interbody/intravertebral body device 28a may also act as an artificial disk allowing movement.

Figure 4:
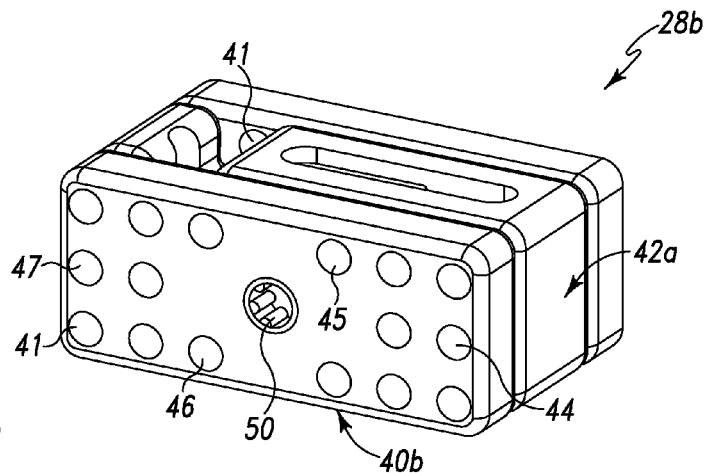
FIG. 4 is a perspective view of an exemplary embodiment of an expandable interbody/intravertebral body device in accordance with the present principles, the expandable interbody/intravertebral body device depicted in a pre-implant or unexpanded state.
Figure 5:
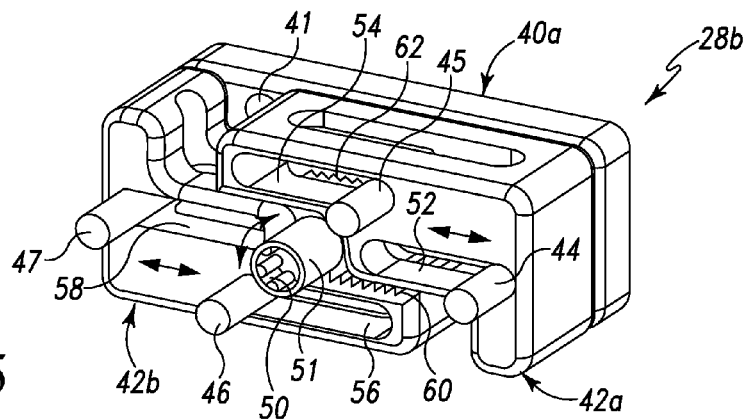
FIG. 5 is a perspective view of the expandable interbody/intravertebral body device of FIG. 4 depicted in the pre-implant or unexpanded state with a plate thereof removed for viewing of an expansion mechanism thereof.
Figure 6:
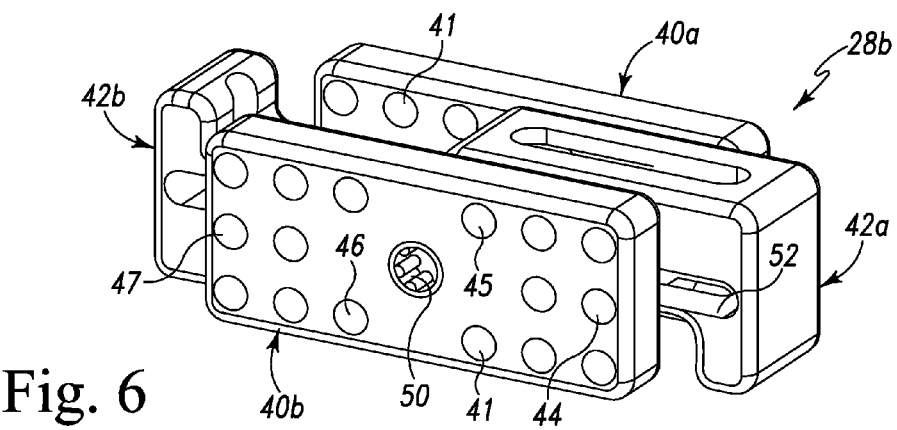
FIG. 6 is a perspective view of the expandable interbody/intravertebral body device of FIG. 4 depicted in a post-implant or expanded state.

Referring to FIGS. 4-6 there is depicted an embodiment of an expandable and retractable (dynamic) interbody/intravertebral body device generally designated 28b. FIG. 4 depicts the interbody/intravertebral body device 28b in a fully unexpanded or fully retracted position, while FIG. 6 depicts the interbody/intravertebral body device 28b in a fully expanded or fully un-retracted position. Of course, the interbody/intravertebral body device 28b may be positioned anywhere between the fully expanded to fully refracted positions. FIG. 5 depicts the manner in which the interbody/intravertebral body device 28b expands. Thus, in FIG. 5 the end plate 40b is removed for clarity in illustrating such expansion (and oppositely, contraction).

The interbody/intravertebral body device 28b is an anterior inserted interbody/intravertebral body device that provides controlled, horizontal expansion within the intervertebral space 26 as well as vertical retraction within the intervertebral space 26. The interbody/intravertebral body device 28b includes identical end plates 40a, 40b each having holes or bores 41 therein. The end plates 40a, 40b are joined together via posts 44, 45, 46 and 47. The posts 44, 45, 46 and 47 also provide a guide for the identical expansion/retraction members 42a and 42b that are retained between the end plates 40a, 40b.

Particularly, member 42a has a first slot 52 in which post 44 is situated, and a second slot 54 in which post 45 is situated. The slots and posts define the length of travel for the member 42a when the keyed shaft 50 is rotated. As well, the member 42b has a first slot 56 in which post 46 is situated, and a second slot 58 in which post 47 is situated. The slots and posts define the length of travel for the member 42b when the keyed shaft 50 is rotated.

The shaft 50 includes knurls or teeth 51 on an outside thereof that co-act with teeth 60 of member 42a and teeth 62 of the member 42b. Rotation of the shaft 50 in a first radial direction moves the members 42a and 42b in opposite and outward direction. Rotation of the shaft 50 in a second direction (opposite the first direction) moves the members 42a and 42b inwardly.

Referring to FIGS. 7-13 there is depicted another embodiment of an interbody/intravertebral body device generally designated 28c. The interbody/intravertebral body device 28c is shown in a pre-implant or unexpanded/collapsed state in FIGS. 7-10 and in a post-implant or expanded state in FIGS. 11-13. The interbody/intravertebral body device 28c is characterized by a body 70 having a first end plate 72 and a second end plate 74. The first end plate 72 includes a plurality of grips or spikes 73. The second end plate 74 also includes a plurality of grips or spikes 75. The spikes 73, 75 are shown as cone-shaped but may take on other forms. The spikes 73, 75 are designed to grip or extend into adjacent vertebrae.

The interbody/intravertebral body device 28c also includes a first side component 76 and a second side component 78. The first end plate 72 is pivotally connected at one side thereof to the first side component 76 by a first hinge component 93 via hinge plates 86 and 87 of the first hinge component 93, and pivotally connected at another side thereof to the second side component 78 by a second hinge component 94 via hinge plates 84 and 85 of the second hinge component 94. In like manner, the second end plate 74 is pivotally connected at one side thereof to the first side component 76 by a third hinge component 91 via hinge plates 82 and 83 of the third hinge component 91, and pivotally connected at another side thereof to the second side component 78 by a fourth hinge component 92 via hinge plates 80 and 81 of the fourth hinge component 92.

The interbody/intravertebral body device 28c further includes an expansion/contraction member (threaded shaft or screw) 90 that extends through a bore 88 of the second side component 78 and into the head 77 associated with the first side component 76. Expansion of the interbody/intravertebral body device 28c from the collapsed position as depicted in FIGS. 7-10 to the fully expanded position depicted in FIGS. 11-13 is accomplished by pushing the first and second side components 76 and 78 towards each other. As the threaded shaft 90 is rotated, the first and second side components 76, 78 are drawn towards one another. This pivots the first and second end plates 72 and 74 away from each other via the first, second, third and fourth hinge components 93, 94, 91, and 92 respectively.

The interbody/intravertebral body device 28c may be dimensioned as necessary. However, currently it has been found that an optimum implant footprint is approximately 6.35 mm by 9.00 mm. Moreover, the interbody/intravertebral body device 28c is preferably, but not necessarily, dimensioned to have an optimal distraction of 16.00 mm and a maximum distraction of 22.00 mm. As such, the interbody/intravertebral body device 28c is deliverable (implantable) via a minimally invasive tube delivery (e.g. 8 mm tube delivery). Furthermore, the expansion member (e.g. screw) is designed to be a torque limiting break-away screw.

Figure 14:
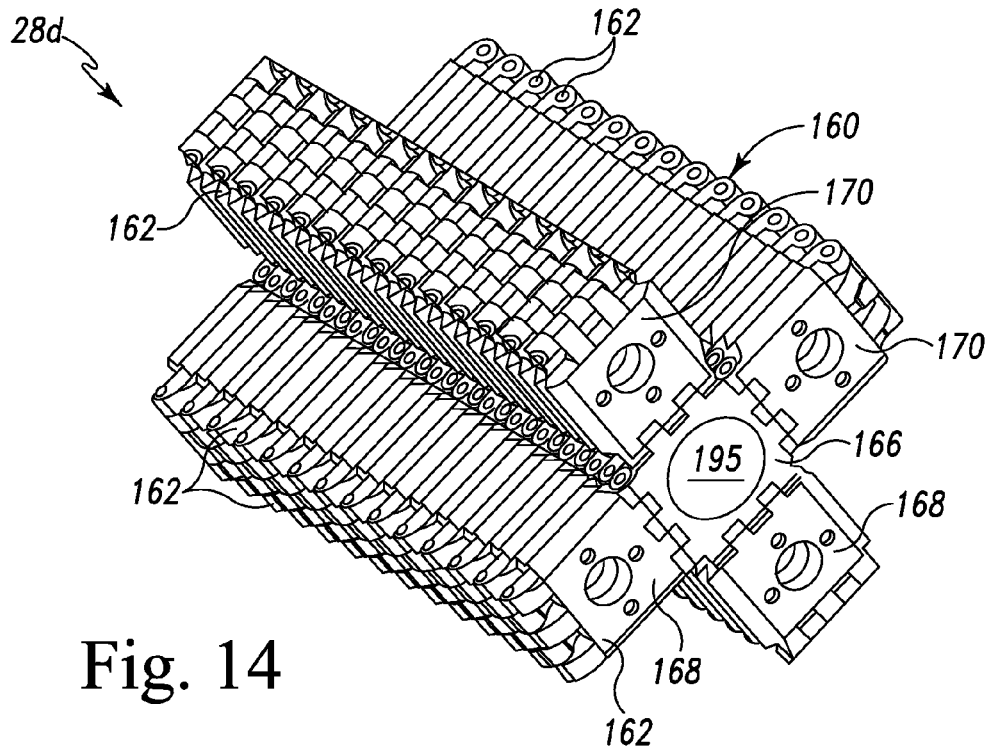
FIG. 14 is front a perspective view of an exemplary embodiment of an expandable interbody/intravertebral body device in accordance with the present principles, the interbody/intravertebral body device shown in a post-implant or expanded state.
Figure 15:
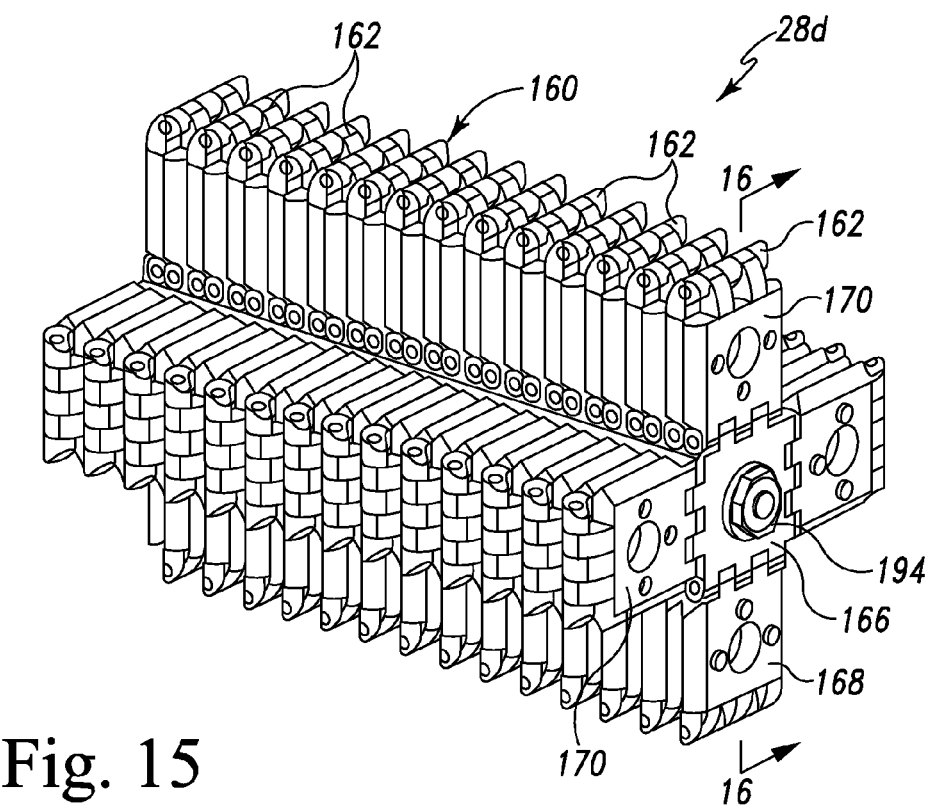
FIG. 15 is a rear perspective view of the expandable interbody/intravertebral body device of FIG. 14.
Figure 18:
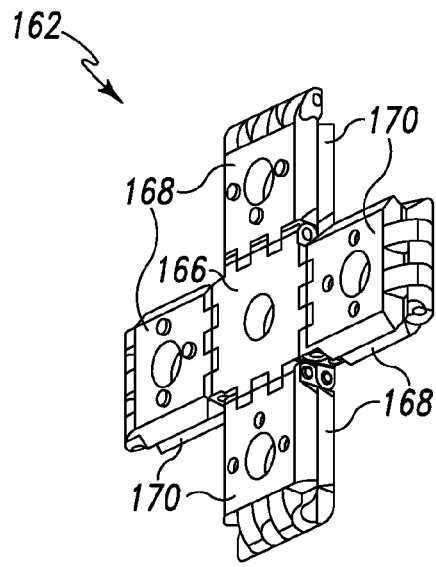
FIG. 18 is a perspective view of the single segment of FIG. 17.
Figure 19:
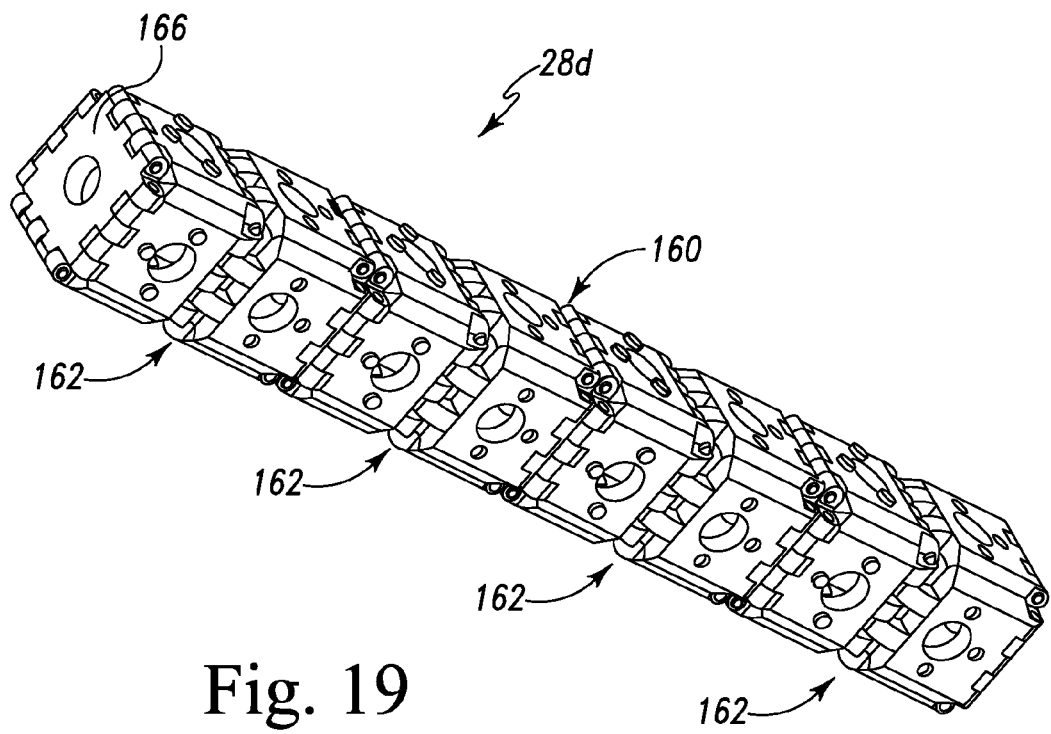
FIG. 19 is a perspective view of a plurality of expandable interbody/intravertebral body segments axially situated one to another forming an implant, the segments shown in a pre-implant or unexpanded state.

Referring to FIGS. 14-22 there is depicted another dynamic interbody/intravertebral body device generally designated 28d. The interbody/intravertebral body device 28d is characterized by a body structure 160 formed by a plurality of dynamic (expands and contracts) sections or portions 162. In FIGS. 14-16, the interbody/intravertebral body device 28d is shown in an expanded or (post) implanted state. In FIG. 19, the interbody/intravertebral body device 28d is shown in a collapsed, folded or pre implant state. In like manner, FIG. 18 depicts one section 162 in an expanded state Each section 162 is formed from three basic plates or components; i.e. an end plate 166 (see FIG. 20) used as a front plate and a back plate, a first inter-connect plate 168 (see FIG. 71) used as type I side plates, and a second inter-connect plate 170 (see FIG. 72) used as type II side plates. The various plates 166, 168 and 170 are pivotally or hingedly coupled to one another to form a section 162 such that the unexpanded box-like structure of each section collapses or folds into an expanded state.

Referring specifically to FIG. 20, end plate 166 is characterized by a rectangular and preferably, but not necessarily, generally square body 167 having a central bore 172. The body 167 includes a plurality of like hinge flanges 174 each having a hinge bore 175 therethrough for receiving a hinge pin. The body 167 includes a first side having three hinge flanges 174, a second side adjacent the first side and having three hinge flanges 174, a third side adjacent the second side (and opposite the first side) and having two hinge flanges 174, and a fourth side adjacent the third and first sides (and opposite the second side) and having two hinge flanges 174.

Referring specifically to FIG. 21, first inter-connect plate 168 is characterized by a rectangular and preferably, but not necessarily, generally square body 169 having a central bore 176. The body 169 includes two hinge flanges 178 of a first configuration each having a hinge bore 179 therethrough for receiving a hinge pin. The two hinge flanges 178 are disposed on one side of the body 169. The body 169 also includes three hinge flanges 180 of a second configuration each having a hinge bore 181 therethrough for receiving a hinge pin disposed on a side of the body 169 opposite the two hinge flange side. Additionally, the body 169 includes a plurality (here shown as three) semi-perf locaters 182 having a raised portion on one side and an indentation on the other side.

Referring specifically to FIG. 22 second inter-connect plate 170 is characterized by a rectangular and preferably, but not necessarily, generally square body 171 having a central bore 184. The body 171 includes two hinge flanges 186 of a first configuration each having a hinge bore 187 therethrough for receiving a hinge pin. The two hinge flanges 186 are disposed on one side of the body 171. The body 171 also includes three hinge flanges 188 of a second configuration each having a hinge bore 189 therethrough for receiving a hinge pin disposed on a side of the body 171 opposite the two hinge flange side. Additionally, the body 171 includes a plurality (here shown as three) semi-perf locaters 190 having a raised portion on one side and an indentation (seen in FIG. 22) on the other side. The semi-perf locators help lock the parts together when the section is expanded. Holes and taper pins may also be used.

The expandable interbody/intravertebral body device 28d may be termed a quad directional interbody/intravertebral body device (e.g. fusion cage) or intervertebral device (e.g. interbody/intravertebral body) that is constructed with interlocking, hinged segments. The expandable interbody/intravertebral body device 28d has an implant footprint (distraction size) of 18.00 mm×18.00 mm (for a size 7 inner segment size). The expandable interbody/intravertebral body device 28d provides push action delivery. A minimally invasive (8 mm) tube delivery may be used. Segments or sections (262) may be added as needed. Preferably, the interbody/intravertebral body device 28d is fashioned from all titanium, but may be fashioned from other biocompatible material. When distracted, there is a 2 mm segment width. The interbody/intravertebral body device 28d may be provided in various sizes ranging from a size 1 through a size 7 with the size 1 having an inner segment size of 4.44 mm and distraction size of 12.00 mm, the size 2 having an inner segment size of 4.81 mm and distraction size of 13.00 mm, the size 3 having an inner segment size of 5.18 mm and distraction size of 14.00 mm, the size 4 having an inner segment size of 5.55 mm and distraction size of 15.00 mm, the size 5 having an inner segment size of 5.92 mm and distraction size of 16.00 mm, the size 6 having an inner segment size of 6.29 mm and distraction size of 17.00 mm, and the size 7 having an inner segment size of 6.66 mm and distraction size of 18.00 mm.

After insertion of the pre-implant structure, a threaded rod 192 having retained the pre-implant structure together during implantation via a head 195, is drawn out by a tool inserted into bore 193 to force the sections 162 to collapse and thus expand. A nut 194 is threadedly received on an exposed end of the rod 192 to retain the body 160 in the expanded state.

Referring to FIGS. 23-51 there is depicted another embodiment of an expandable vertebral interbody/intravertebral body device generally designated 28e. The expandable interbody/intravertebral body device 28e is radially expandable upon axial compression. Radial expansion provides vertical (co-spinal) height within a vertebral body area (see e.g. FIG. 1 area 26). Thus, the interbody/intravertebral body device 28e is characterized by the ability to be inserted or implanted into an open vertebral space in a folded or unexpanded, radially compact state or position and then be unfolded or expanded. The interbody/intravertebral body device 28e is formed of titanium, stainless steel or other biocompatible material, including composites, plastics and/or the like. Radiolucent materials may also be used and, the interbody/intravertebral body device 28e (as well as the other interbody/intravertebral body devices herein) may be formed entirely of a radiolucent material.

Figure 23:
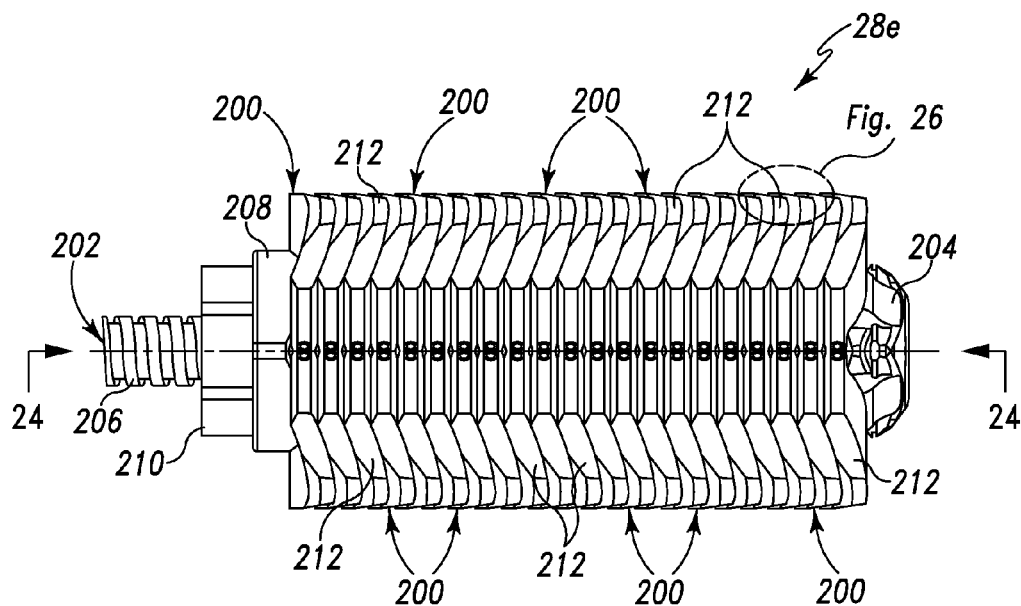
FIG. 23 is a side view of an exemplary embodiment of an expandable interbody/intravertebral body device in accordance with the present principles, the expandable interbody/intravertebral body device shown in a post-implant or expanded state.
Figure 24:
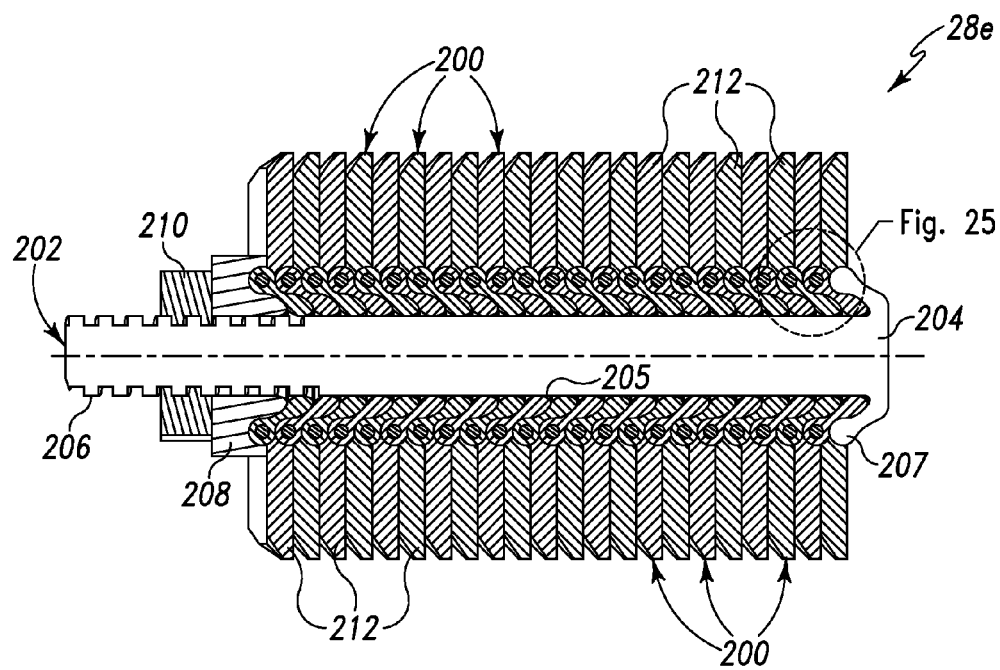
FIG. 24 is a cross-sectional view of the expandable interbody/intravertebral body device of FIG. 23 taken along line 24-24 thereof.
Figure 27:
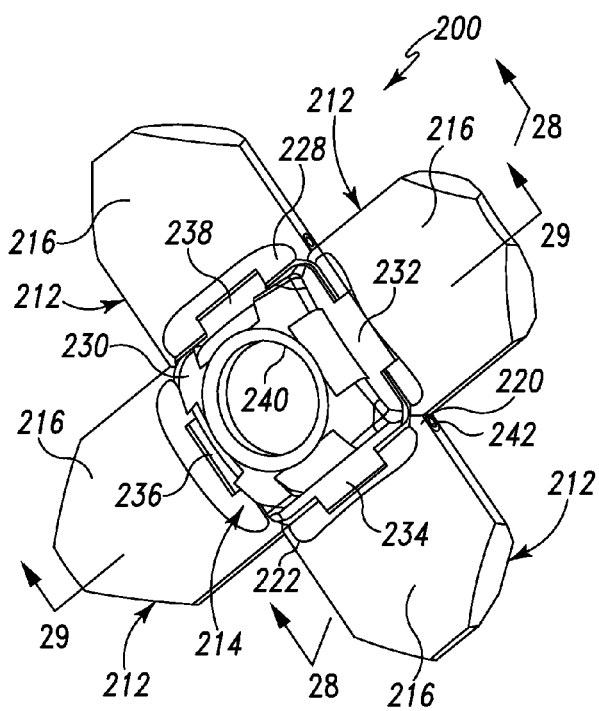
FIG. 27 is an enlarged perspective view of a segment or section of the expandable interbody/intravertebral body device of FIG. 23 in an expanded state.
Figure 30:
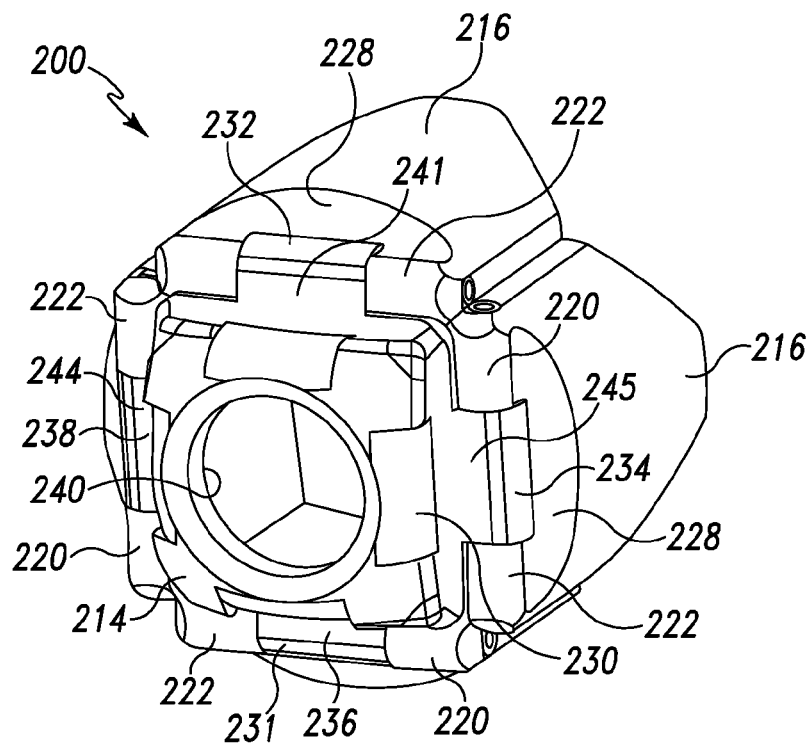
FIG. 30 is an enlarged perspective view of the interbody/intravertebral body segment of FIG. 27 shown in a folded or retracted state.
Figure 46:
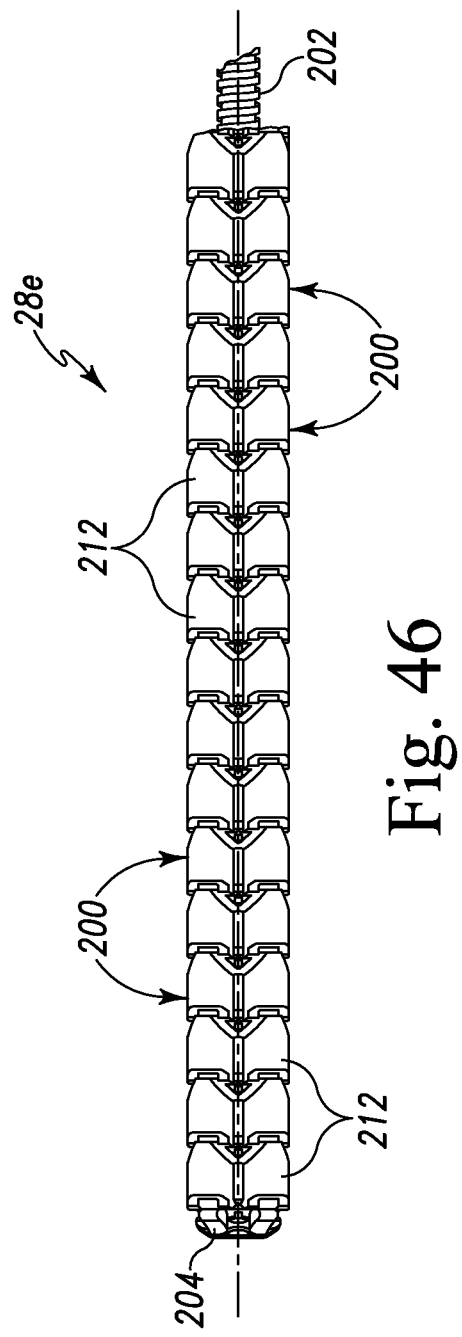
FIG. 46 is a side view of the expandable interbody/intravertebral body device of FIG. 23 in a folded position.

The interbody/intravertebral body device 28e is shown in an expanded position in FIGS. 23 and 24. The interbody/intravertebral body device 28e is characterized by a plurality of segments or sections 200 that each individually expand from a collapsed or unexpanded position into an extended or expanded position to form a vertebral interbody/intravertebral body device. FIG. 46 depicts the interbody/intravertebral body device 28e in a collapsed, folded or pre-deployment position such as after being assembled for introduction or insertion into a vertebral space. FIG. 27 depicts a segment 200 in an expanded or open position such as is seen in FIGS. 23 and 24. FIG. 30 depicts a segment 200 in a collapsed or folded position. The expandable vertebral interbody/intravertebral body device 28e is thus composed of a plurality of segments 200, the number and width thereof defining the overall axial length of the interbody/intravertebral body device 28e when expanded, with the number and axial length of leaves 212 (see, e.g. FIGS. 37-41) of the segments 200 defining the overall radial height of the interbody/intravertebral body device 28e when expanded.

The plurality of segments 200 is carried on an insertion and deployment rod 202. A deploy head or cap 204 is provided at the end of the rod 202 and is preferably integral therewith. The deploy head 204 is configured to engage, cooperate and interact with a central or middle deploy plate 214 of the segment 200. Particularly, a flange structure 207 of the rod 202 engages respective grooves (see FIG. 35 wherein three grooves 241, 244 and 245 of the four grooves of the deploy plate 214 are shown) of the deploy plate 214 (see also FIG. 25). The flange structure 207 represented in FIG. 24 is illustrated in FIGS. 42 and 43. The flange structure of the head 204 consists of four flanges 269, 270, 271 and 272 carried on a rectangular body 266. The four flanges are respectively received in the four grooves of the deploy plate 214. As described further below, axial compression of the deploy plate of the segment and the head of the rod causes the leaves 212 to pivot from an axial position to a position perpendicular to the axial position.

As best seen in FIG. 42, the rod 202 has a threaded shaft portion 206 and a non-threaded shaft portion 205. The non-threaded shaft portion 205 allows the segments 200 to axially slide during expansion of the segments 200. The threaded portion 206 threaded receives the nut 210 allows it to provide the axial force for axial compression of the segments 200 and the expansion thereof.

An end cap 208 is provided on the rod 202 distal from the head 204 of the rod 202 and between the nut 210 and the last (from left to right) deploy plate 214 of the last segment 200. The end cap 208 abuts against the central deploy plate 214 of the last segment 200. The nut 210 abuts the end cap 208. Particularly, the end cap 208 has four grooves 249, 251, 253 and 255 (see FIG. 33) that correspond to the four tubular flanges or hinge structures (which will be referred to as tubular hinge structures 232, 234, 236 and 238) of the central deploy plate 214. The tubular hinge structures of the deploy plate 214 are nested or received into the grooves of the end plate 208. Moreover, a threaded nut 210 is provided on the rod 202 to provide axial compression of the segments 200 when threadedly advanced toward the head 204 of the rod 202 to achieve radial expansion of the interbody/intravertebral body device 28e. This is done after proper placement of the interbody/intravertebral body device 28e into a vertebral space 26.

Figure 33:
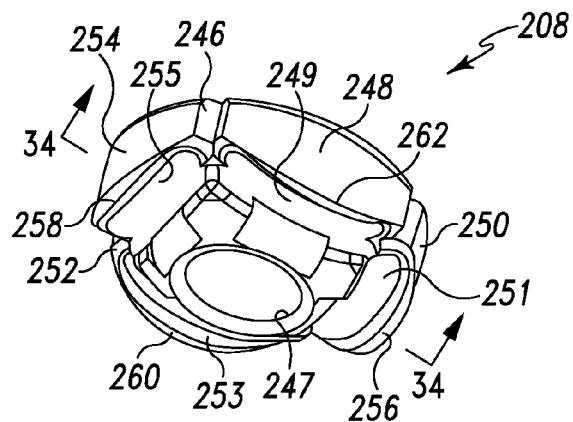
FIG. 33 is a perspective view of an end plate of the expandable interbody/intravertebral body device of FIG. 23.
Figure 34:
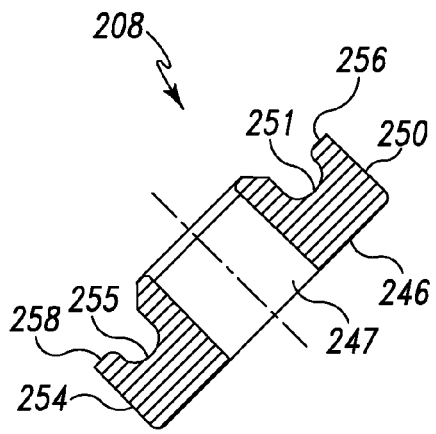
FIG. 34 is a sectional view of the end plate of FIG. 33 taken along line 34-34 thereof.

As seen in FIGS. 33 and 34, the end cap 208 is particularly characterized by a body 246 having a central or middle bore 247 that is sized to be received onto the rod 202. The body 246 defines four flanges 248, 250, 252 and 254 on sides thereof. The four flanges 248, 250, 252 and 254 each defining a respective groove 249, 251, 253 and 255 and a respective contact surface 262, 256, 260 and 258. The grooves 249, 251, 253 and 255 providing a contact surface for the tubular hinge structures 232, 234, 236 and 238 of the deploy plate 214.

Figure 26:
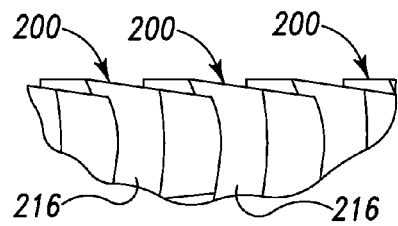
FIG. 26 is an enlarged portion of the side view of the expandable interbody/intravertebral body device of FIG. 23.
Figure 25:
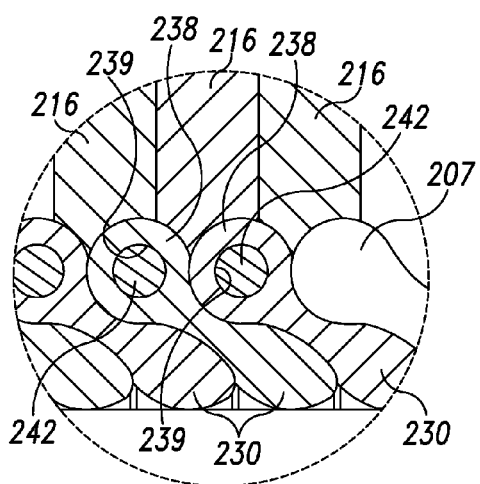
FIG. 25 is an enlarged portion of the sectional view of the expandable interbody/intravertebral body device of FIG. 24.
Figure 28:
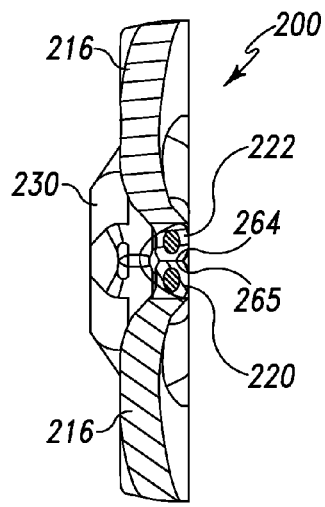
FIG. 28 is a sectional view of the interbody/intravertebral body segment of FIG. 27 taken along line 28-28 thereof.
Figure 29:
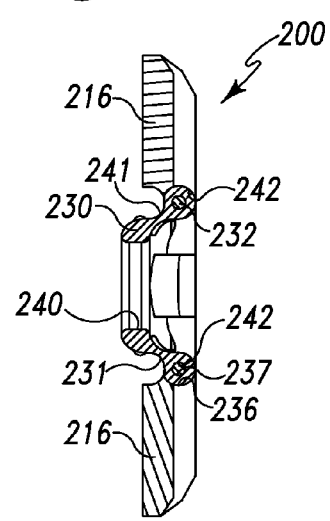
FIG. 29 is a sectional view of the interbody/intravertebral body segment of FIG. 28 taken along line 29-29 thereof.
Figure 31:
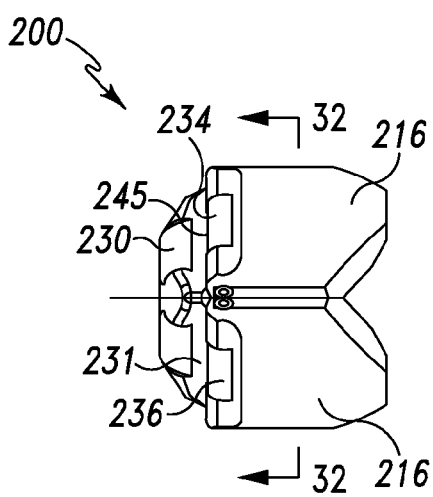
FIG. 31 is a side view of the folded interbody/intravertebral body segment.
Figure 32:
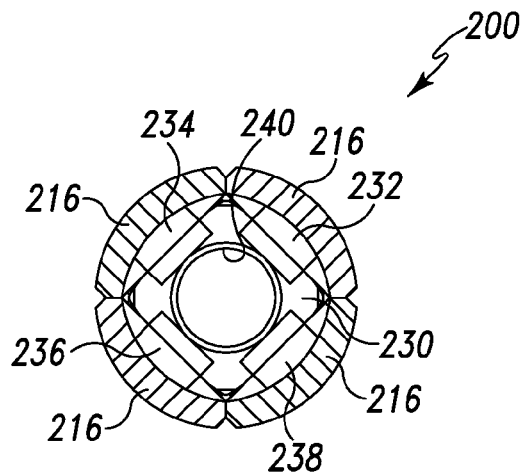
FIG. 32 is a sectional view of the folded interbody/intravertebral body segment of FIG. 31 taken along line 31-31 thereof.

As seen in FIGS. 27-32, the segments 200 include the middle or central deploy plate 214 (see FIG. 33) to which are pivotally, hingedly or swingably attached a plurality (here, four) leaf structures 212. The leaf structures 212 are pivotally attached to the deploy plate 214 by hinge pins 242 and are structured to provide a collapsed or folded position as seen in FIGS. 30-32 wherein a longitudinal axis of each leaf structure 212 is essentially co-axial with the rod 202, and an expanded or open position as seen in FIGS. 27-29 where the longitudinal axis of each leaf structure 212 is essentially perpendicular to the longitudinal axis of the rod 202. The folded position of the segments 200 provide a small diameter device, while the expanded position of the segments 200 provides a larger diameter device constrained by the length of the leaf structures 212. As illustrated in FIG. 26, the leaf bodies 216 of the segments 200 form a toothed, stepped or jagged profile.

Figure 35:
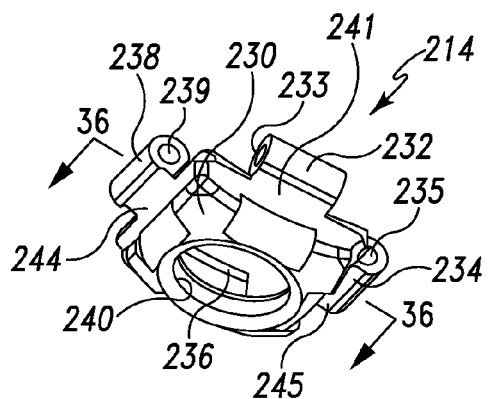
FIG. 35 is a perspective view of a deploy plate of the interbody/intravertebral body segment of the expandable interbody/intravertebral body device of FIG. 23.
Figure 36:
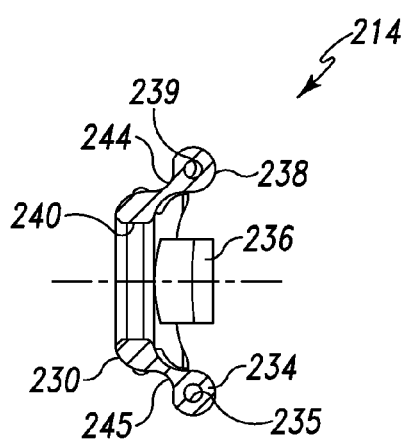
FIG. 36 is a sectional view of the deploy plate of FIG. 35 taken along line 36-36 thereof.
Figure 37:
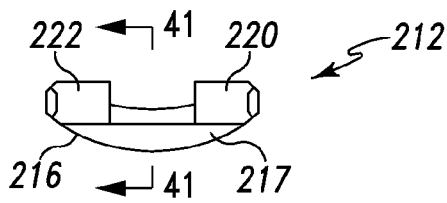
FIG. 37 is a front view of a leaf of the interbody/intravertebral body segment.
Figure 38:
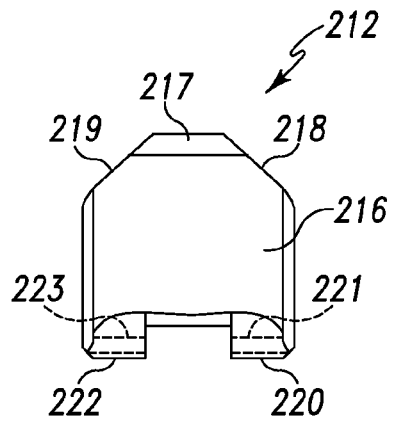
FIG. 38 is a bottom view of the leaf of the interbody/intravertebral body segment.
Figure 39:
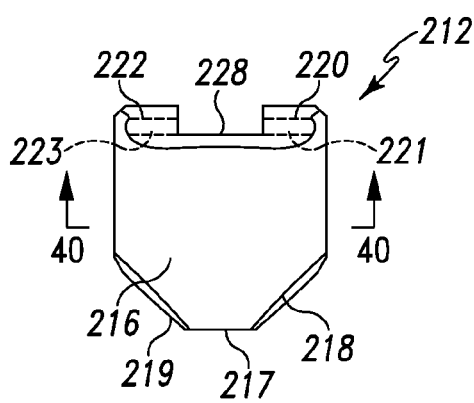
FIG. 39 is a top view of the leaf of the interbody/intravertebral body segment.
Figure 40:
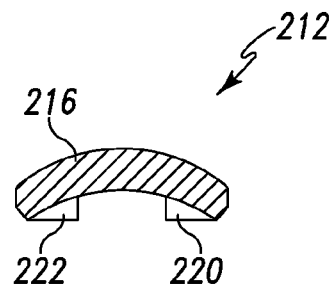
FIG. 40 is a sectional view of the leaf of the interbody/intravertebral body segment taken along line 40-40 of FIG. 39.
Figure 41:
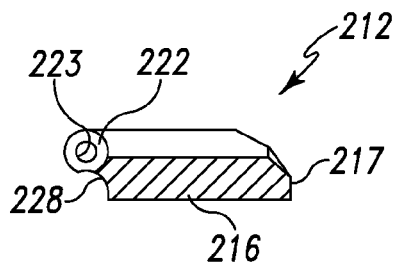
FIG. 41 is a sectional view of the leaf of the interbody/intravertebral body segment taken along line 41-41 of FIG. 37.

Referring to FIGS. 35 and 36, the deploy plate 214 of a segment 200 is particularly shown. The deploy plate 214 is characterized by a generally rectangular body 230 having a central or middle bore 240. The bore 240 is sized to be received onto the rod 202. Four cylindrical or tubular hinge structures 232, 234, 236 and 238 extend from the four sides of the body 230. Each tubular hinge structure 232, 234, 236 and 238 has a bore 233, 235, 237 and 239 respectively for receipt of a pivot pin 242. The body 230 also defines four grooves 241, 245, 231, and 244 adjacent the four hinge structures 232, 234, 236 and 238 respectively.

Referring to FIGS. 37-41 the leaf structure 212 of a segment 200 is particularly shown. A leaf structure 212 consists of a leaf body 216 having a generally "home-plate" shape (see e.g., FIGS. 38, 39) with an arched profile (see e.g., FIGS. 37, 40). As such, the body 216 includes a front 217 and two angled portions 218, 219. First and second tubular or cylindrical pivot flanges 220, 222 are provided on one side 228 of the body 216. The first flange 220 includes a bore 221 for receipt of a pivot pin 242. The second flange 222 includes a bore 223 for receipt of a pivot pin 242. The two flanges 220 and 222 are spaced from one another so as to receive a tubular flange (e.g. hinge structure 232) of the deploy plate body 230 such that the two flanges 220, 222 of the leaf body 216 straddle or are on opposite axial sides of the respective deploy plate tubular flange. In this manner a pivot pin 242 may extend through the flange 220 of the leaf body 216, the tubular flange of the deploy plate body 230, and though the flange 222 of the leaf body 216. When four leaf structures 212 are connected to the middle body 230, the leaf bodies 216 can pivot between a closed, folded or collapsed position (FIG. 30) and an open, extended or expanded position (FIG. 27).

As best seen in FIG. 28, when the leaf structures 212 are expanded, the rounded flanges 220 and 222 and flats 264 and 265 on ends of the flanges 220 and 222 of the leaf body 216 coact to provide a positive or snap feature to lock the leaf structures 212 in the expanded position.

The interbody/intravertebral body/intervertebral body device 28e, like the other interbody/intravertebral body device described herein, are designed to be delivered, installed, implanted or positioned in a patient via a cannula or tube. Such a cannula 274 is illustrated in FIGS. 44 and 45. The cannula 274 is defined by a tubular body 276 having an inner or inside surface 278. Four prongs or protrusions 280, 281, 282 and 283 are provided on the inside surface 278. These serve to guide, orient and allow expansion of the interbody/intravertebral body device 28 during implantation.

Figure 47:
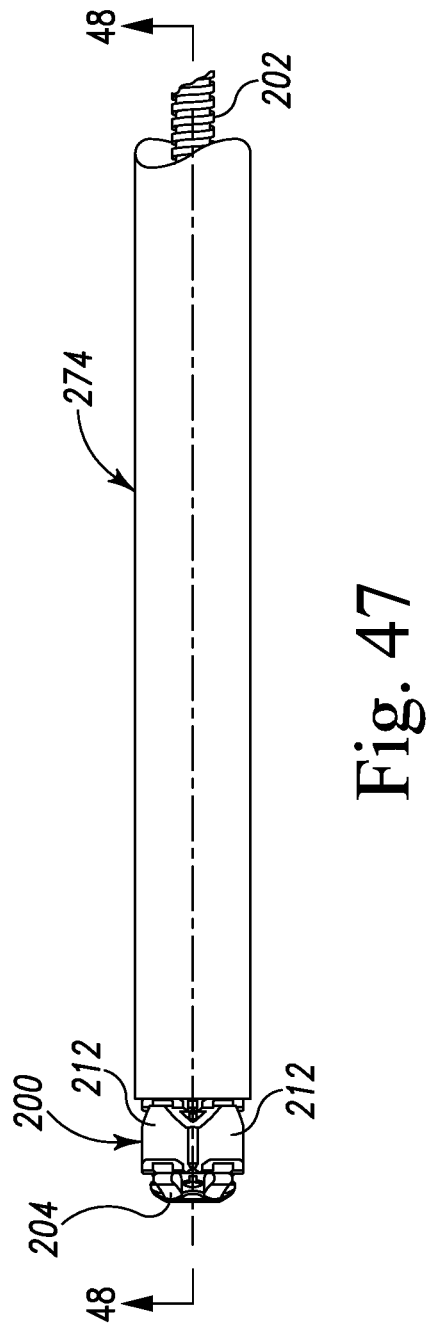
FIG. 47 is a side view of the insertion and deployment cannula of FIG. 45 holding the folded interbody/intravertebral body device of FIG. 46.
Figure 48:
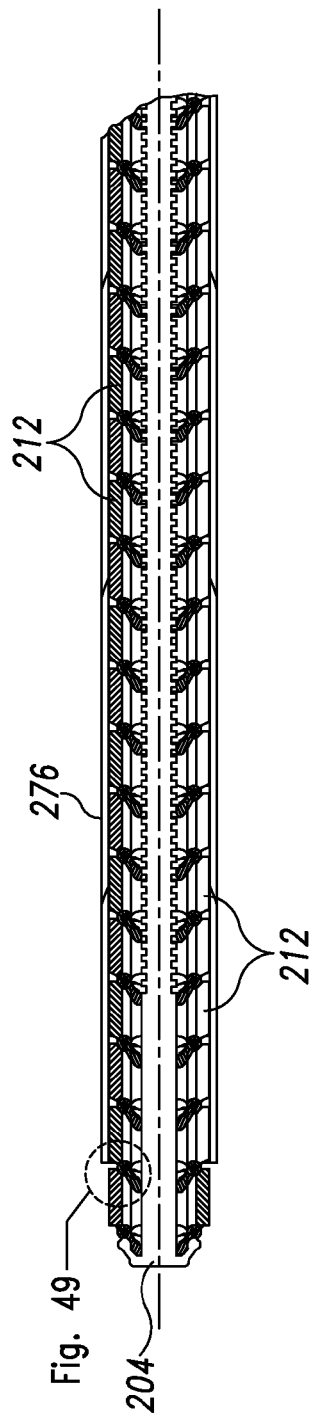
FIG. 48 is a sectional view of FIG. 47 taken along line 48-48 thereof.
Figure 49:
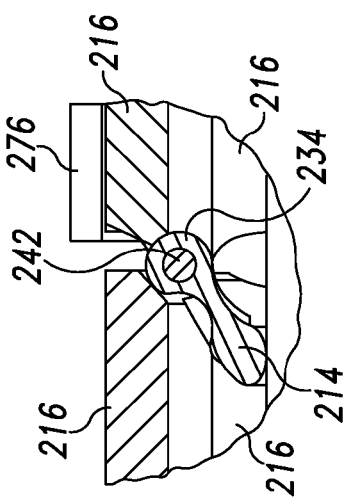
FIG. 49 is an enlarged, sectional portion of FIG. 48.

FIGS. 46-49 provide an illustration of the interbody/intravertebral body device 28e assembled for being implanted in a vertebral space. FIG. 46 shows an interbody/intravertebral body device 28e assembled and in a collapsed position. The number of segments 200 determines the overall axial length of the resulting expanded device. The assembled and collapsed interbody/intravertebral body device is provided in the cannula 274 in FIG. 47. A sectional view of FIG. 47 is provided in FIG. 48. FIG. 49 particularly depicts the juncture of the end of the cannula 274 and a segment 200 of the interbody/intravertebral body device 28e. At this point, a first segment may be deployed (expanded).

Figure 51:
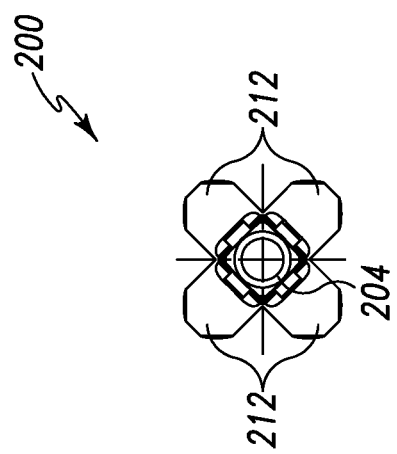
FIG. 51 is an end view of the interbody/intravertebral body device of FIG. 50 taken along line 51-51 thereof.
Figure 50:
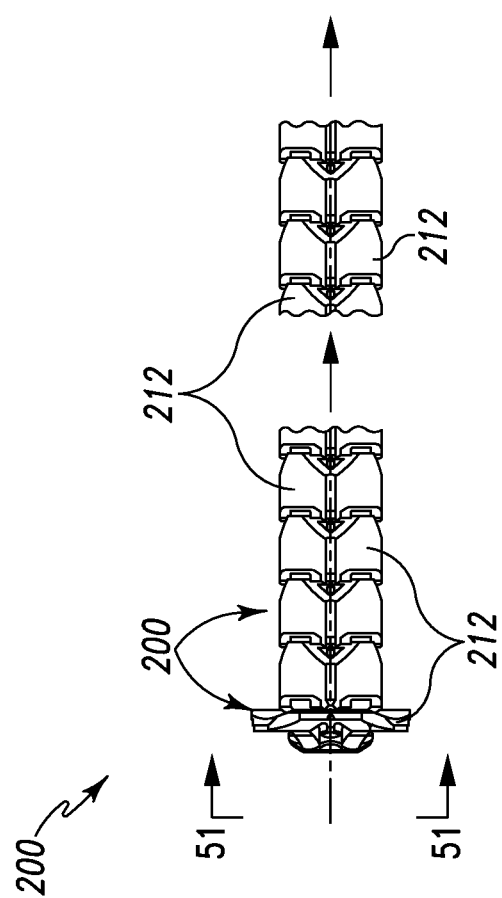
FIG. 50 is a side view of the folded expandable interbody/intravertebral body device of FIG. 46 illustrating deployment thereof.

FIGS. 50 and 51 particularly illustrate how axial compression (represented by the arrows) causes the segments 200 to expand. Particularly, axially compression causes a first segment 200 to expand. Thereafter, each successive segment expands in a somewhat "domino" effect as more axial compression is applied. In this embodiment, axial compression is provided by the nut 210. Thus, when the interbody/intravertebral body device 28e is properly placed, the nut 210 is rotated to provide axial compression until all of the segments 200 are expanded.

Figure 52:
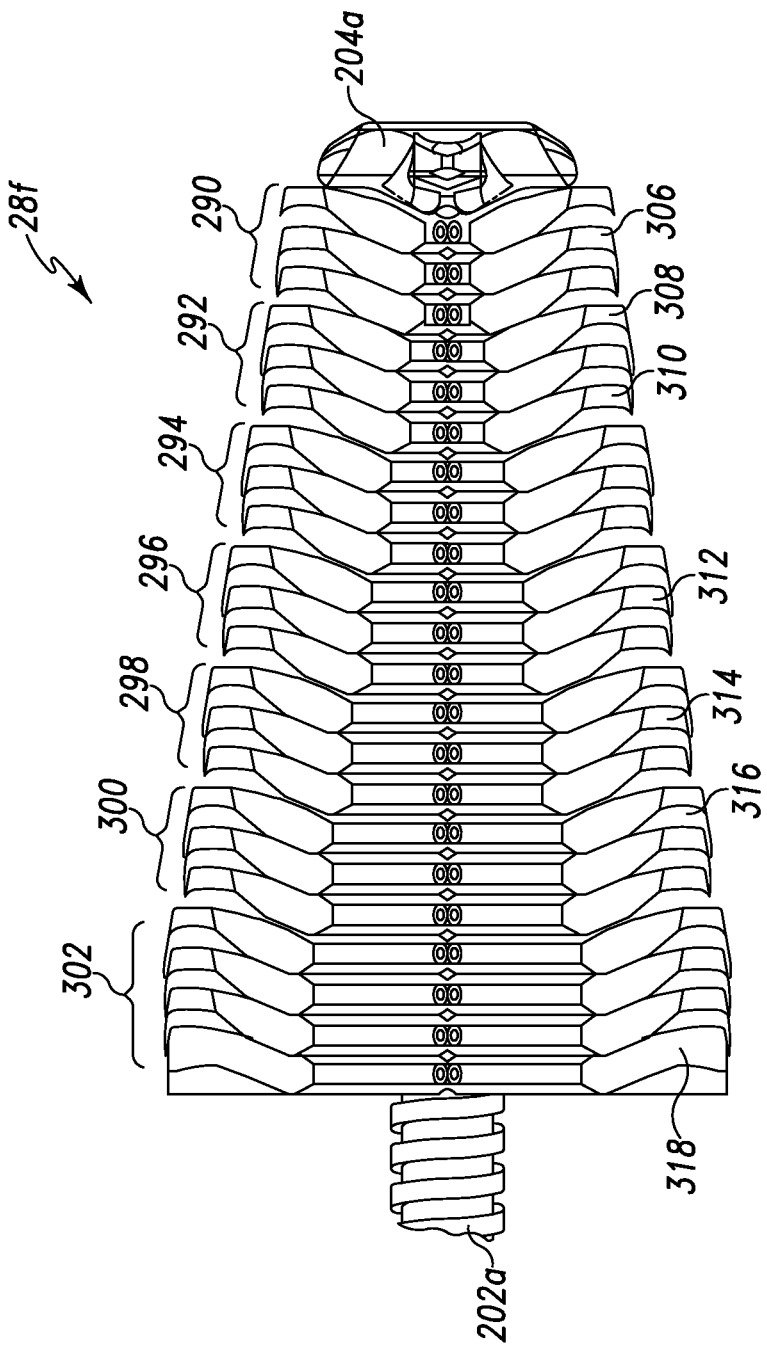
FIG. 52 is a perspective view of an exemplary embodiment of an expandable interbody/intravertebral body device in accordance with the present principles, the interbody/intravertebral body device shown in a post-implant or expanded position.
Figure 53:
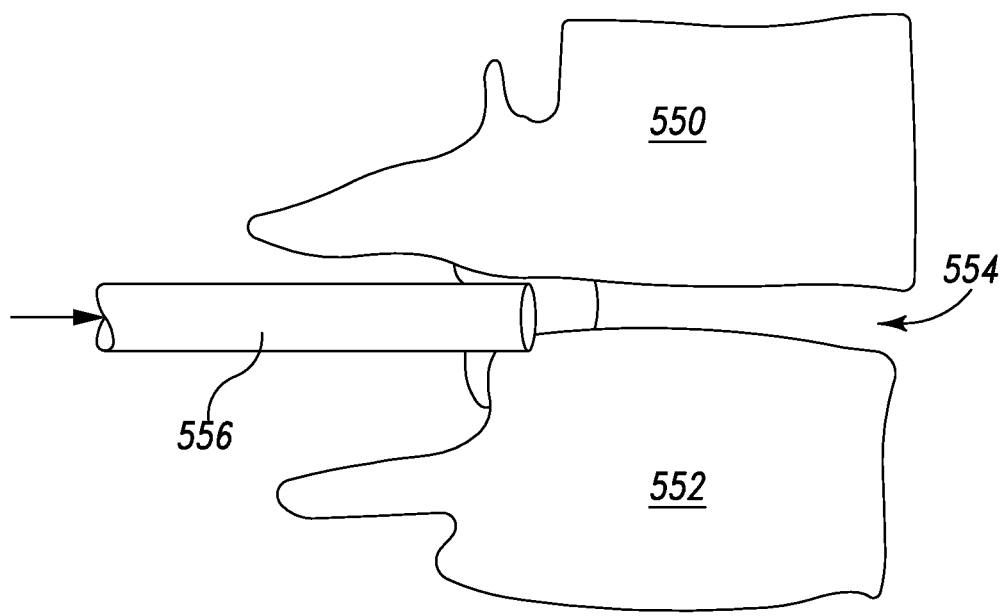
FIG. 53 is a side view of adjacent vertebrae with a cannula (insertion and deployment tube) used to introduce or implant an expandable interbody/intravertebral body device as provided herein.
Figure 54:
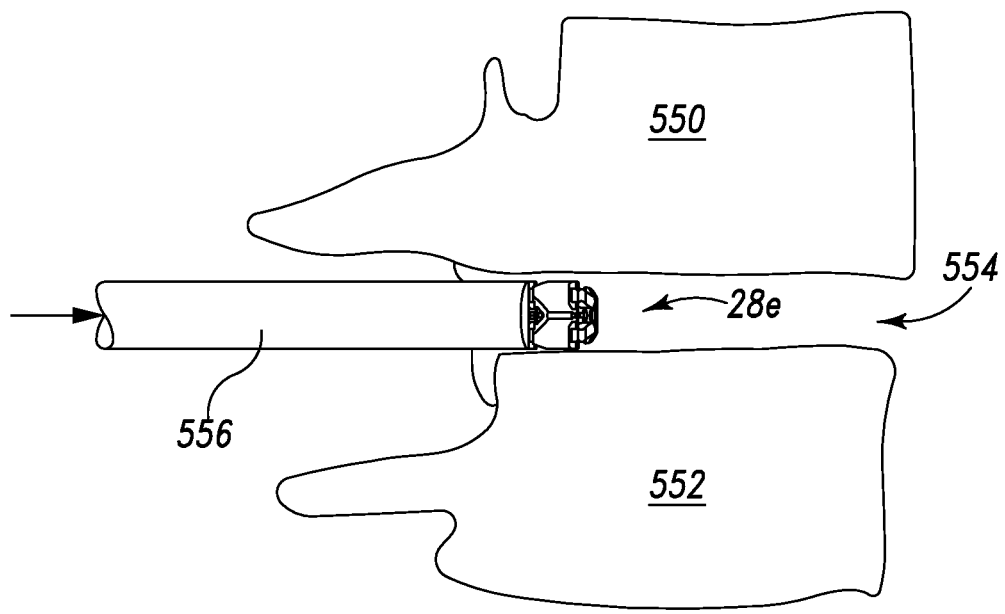
FIG. 54 is the view of FIG. 63 wherein an expandable interbody/intravertebral body device is being inserted between vertebrae.

FIG. 52 depicts an alternative embodiment or variation of the interbody/intravertebral body device 28e illustrating how different radial profiles may be created by using segments of various sizes (dimensions). In FIG. 52 there is depicted a frusto-conically shaped interbody/intravertebral body device generally designated 28f. The interbody/intravertebral body device 28f is shown in a post-implant or expanded state. The interbody/intravertebral body device 28f includes a plurality 290, 292, 294, 296, 298, 300 and 302 of groups of interbody/intravertebral body segments each group of segments 290, 292, 294, 296, 298, 300 and 302 having respective leaves 306, 308, 310, 312, 314, 316 and 318 of different radial height. As can be appreciated, the axial length of any group 290, 292, 294, 296, 298, 300 and 302 is determined by the number of segments in the group. The radial height or profile of each group 290, 292, 294, 296, 298, 300 and 302 is determined by the radial height of the leaf structures (and the middle plate) of the segments. A multitude of radial profiles may be created.

It should be appreciated that the segments 200 of the various interbody/intravertebral body devices may or may not be at least limitedly movable relative to one another. In one case, the segments 200 are fixed relative to each other and therefore no movement can occur between the segments. In another case, the segments 200 are at least limitedly movable radially with respect to another segment 200 such that the interbody/intravertebral body is dynamic. This allows for limited movement within the interbody/intravertebral body device itself.

Figure 55:
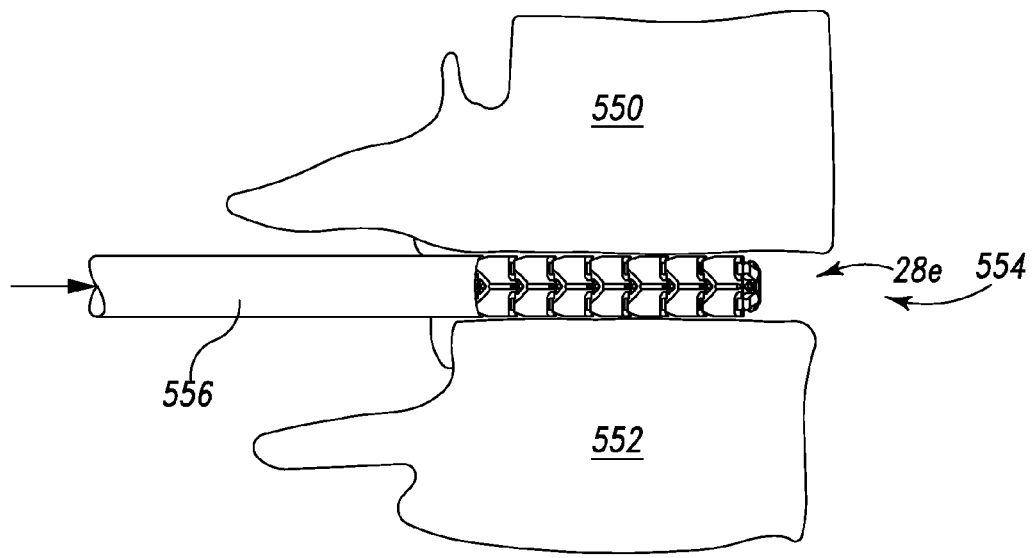
FIG. 55 is the view of FIG. 63 wherein the expandable interbody/intravertebral body device has been properly positioned for expansion/deployment.
Figure 56:
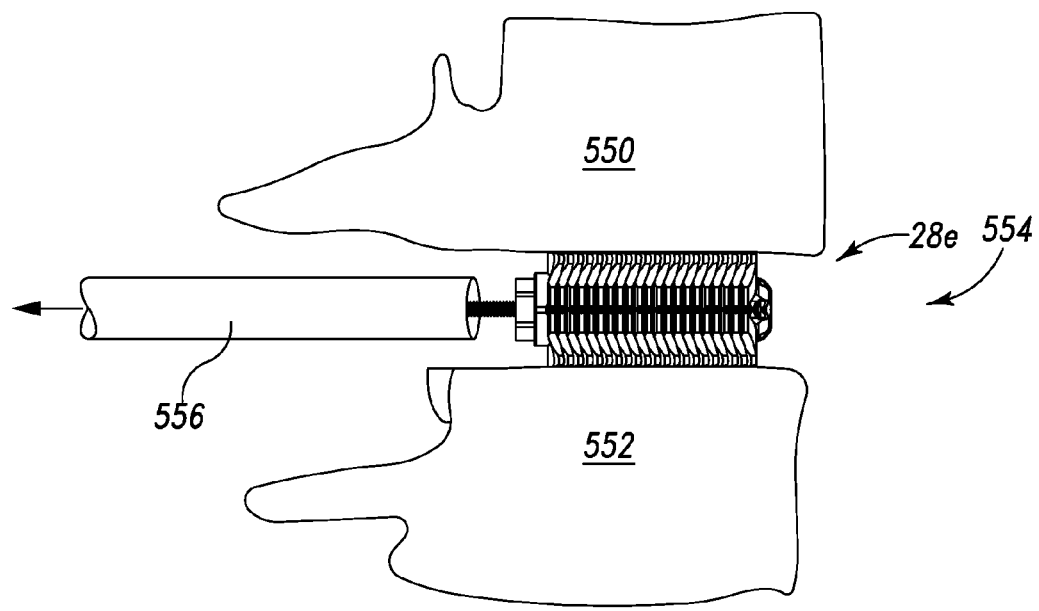
FIG. 56 is the view of FIG. 63 wherein the expandable interbody/intravertebral body device has been fully expanded or deployed.

Referring lastly to FIGS. 53-56, there is illustrated a manner of implanting the interbody/intravertebral body devices 28a-28f. Particularly, but without restriction or being necessarily so, the various interbody/intravertebral body devices 28a-28f are percutaneously implanted via a cannula 556. The end of the cannula 556 is positioned proximate an intervertebral space 554 between a first vertebra 550 and a second vertebra 552. The particular interbody/intravertebral body device (here, interbody/intravertebral body device 28e is shown) is then inserted into the cannula 556 as represented by the arrow. Once the particular interbody/intravertebral body device is appropriately placed in the intervertebral space 554, the interbody/intravertebral body device is expanded via an appropriate instrument through the cannula 556. As shown in FIG. 55 the interbody/intravertebral body device 28e is received in the vertebral space 554. In FIG. 56, the interbody/intravertebral body device 28e has been radially expanded to vertically fill the vertebral space 554 through axial compression of the segments 200 of the interbody/intravertebral body device 28e.

Figure 57:
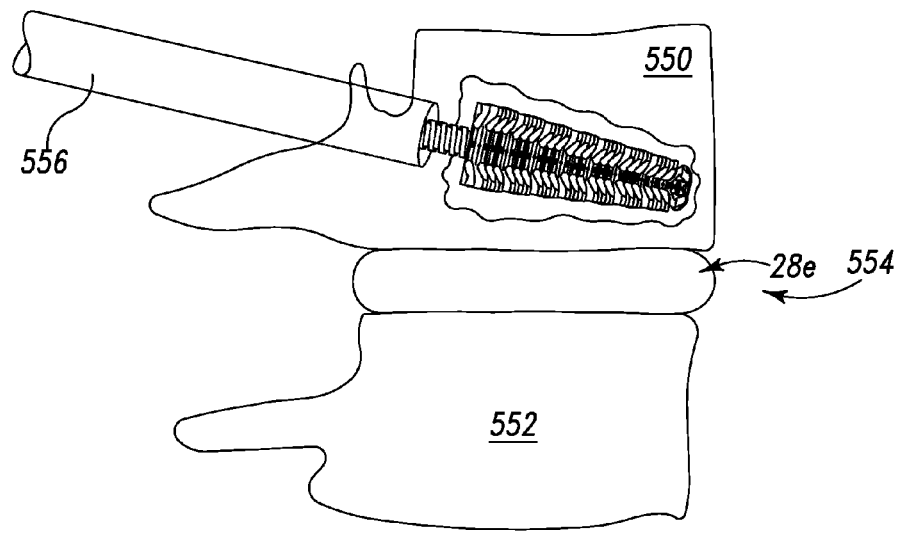
FIG. 57 is side view of a portion of a spinal column showing two adjacent vertebrae with a cannula (insertion and deployment tube) used to introduce or implant an expandable interbody/intravertebral body device as an intravertebral body device, the expandable intravertebral body device shown in an unexpanded position.
Figure 58:
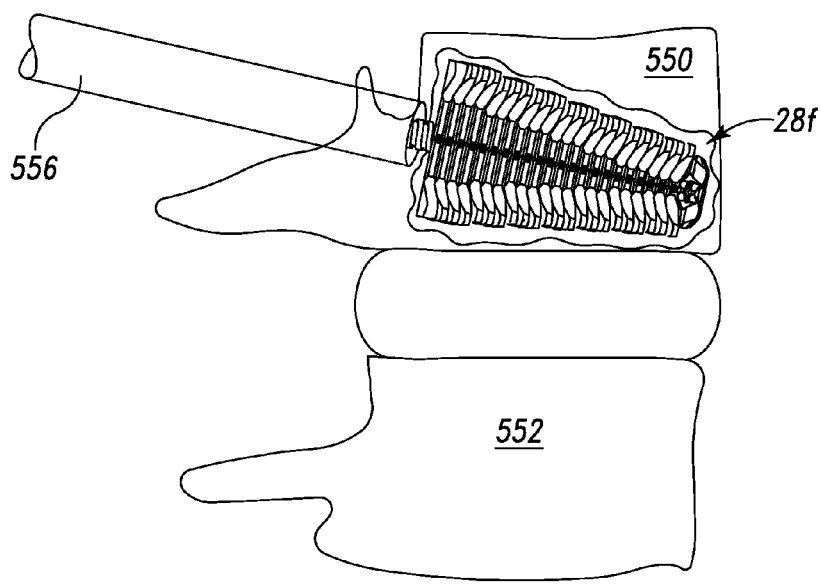
FIG. 58 is the view of FIG. 57 wherein the expandable intravertebral device is shown in an expanded position within the vertebra.

FIGS. 57 and 58 illustrate use of a spinal body 28 as an intravertebral body device. Particularly interbody/intravertebral body 28f is shown in FIG. 57 as implanted via cannula 556 into vertebra 550 (intravertebral). The intravertebral device 28f is initially unexpanded. In FIG. 58, the intravertebral device 28f has been expanded within the vertebra. This use is applicable to treat vertebral compression fractures and/or the like.

It should be appreciated that each interbody/intravertebral body device 28a through 28e may be scaled to any size necessary. Additionally, each interbody/intravertebral body device 28a-28e is manufactured from a bio-compatible material such as a titanium-based metal. Variations are also contemplated.

What is claimed is:

1. An implant for insertion into a spinal space between a first vertebra and a second vertebra, the implant comprising:
a first side component having a first end and a second end;
a second side component having a first end and a second end;
a first end plate having a first end, a second end, and a plurality of grips configured to engage the first vertebra;
a second end plate having a first end, a second end, and a plurality of grips configured to engage the second vertebra;
a first hinge component having a first end and a second end, wherein the first end of the first hinge component is pivotally connected to the first end of the first side component, wherein the second end of the first hinge component is pivotally connected to the first end of the first end plate;
a second hinge component having a first end and a second end, wherein the first end of the second hinge component is pivotally connected to the first end of the second side component, wherein the second end of the second hinge component is pivotally connected to the second end of the first end plate;
a third hinge component having a first end and a second end, wherein the first end of the third hinge component is pivotally connected to the second end of the first side component, wherein the second end of the third hinge component is pivotally connected to the first end of the second end plate;
a fourth hinge component having a first end and a second end, wherein the first end of the fourth hinge component is pivotally connected to the second end of the second side component, wherein the second end of the fourth hinge component is pivotally connected to the second end of the second end plate;

an expansion/contraction member extending through the second side component and coupled to the first side component, wherein the expansion/contraction member comprises a threaded shaft;

wherein a first movement of the expansion/contraction member moves the first side component and second side component toward each other and moves the first end plate and the second end plate away from each other and toward an expanded position;

wherein a second movement of the expansion/contraction member moves the first side component and second side component away from each other and moves the first end plate and the second end plate toward each other and toward an unexpanded position.

2. The implant of claim 1, wherein the expansion/contraction member defines an axis, wherein the first side component and second side component move parallel to the axis, wherein the first end plate and the second end plate move perpendicular to the axis.

3. The implant of claim 1, wherein the first end plate and the second end plate are spaced apart at a dimension greater in the expanded position than in the unexpanded position.

4. The implant of claim 1, wherein the threaded shaft is threadably engaged with the second side component.

5. The implant of claim 4, wherein the movement of the expansion/contraction member comprises rotation of the threaded shaft.

6. The implant of claim 5, wherein the expansion/contraction member comprises a head coupled to the threaded shaft and abutting the first side component.

7. The implant of claim 1, wherein movement of the first side component and second side component pivots the first and second hinge components relative to the first end plate, and pivots the third and fourth hinge components relative to the second end plate.

8. The implant of claim 1, wherein the first hinge component is perpendicular to the axis when the first and second end plates are in the expanded position.

9. A method of introducing the implant of claim 1 into an intervertebral or intravertebral space between a first vertebra and a second vertebra, the method comprising the steps of:
    providing the implant;
    inserting the implant in an unexpanded position into a cannula;
    positioning an opening of the cannula adjacent the vertebral space;
    extending the implant out of the cannula and into the vertebral space;
    providing a first movement to the expansion/contraction member to move the first side component and second side component toward each other and to move the first end plate and the second end plate away from each other toward an expanded position.

10. The implant of claim 9, wherein the first side component and second side component move parallel to the axis defined by the expansion/contraction member, wherein the first end plate and the second end plate move perpendicular to the axis.

11. The implant of claim 10, wherein the expansion/contraction member comprises a threaded shaft threadably engaged with the second side component, and the step of providing the first movement to the expansion/contraction member comprises rotating the threaded shaft.

12. The method of claim 9, further comprising providing a second movement of the expansion/contraction member to move the first side component and second side component away from each other and to move the first end plate and the second end plate toward each other and toward an unexpanded position.

13. An implant for insertion into a spinal space between a first vertebra and a second vertebra, the implant comprising:
    a first side component having a first end and a second end;
    a second side component having a first end and a second end;
    a first end plate having a first end and a second end;
    a second end plate having a first end and a second end;
    a first hinge component having a first end and a second end, wherein the first end of the first hinge component is pivotally connected to the first end of the first side component, wherein the second end of the first hinge component is pivotally connected to the first end of the first end plate;
    a second hinge component having a first end and a second end, wherein the first end of the second hinge component is pivotally connected to the first end of the second side component, wherein the second end of the second hinge component is pivotally connected to the second end of the first end plate;
    a third hinge component having a first end and a second end, wherein the first end of the third hinge component is pivotally connected to the second end of the first side component, wherein the second end of the third hinge component is pivotally connected to the first end of the second end plate;
    a fourth hinge component having a first end and a second end, wherein the first end of the fourth hinge component is pivotally connected to the second end of the second side component, wherein the second end of the fourth hinge component is pivotally connected to the second end of the second end plate;
    an expansion/contraction member defining an axis and extending through the second side component and coupled to the first side component, the expansion/contraction member having a threaded shaft and a head, the threaded shaft threadably engaged with the second side component and the head coupled to the threaded shaft and abutting the first side component;
    wherein rotation of the threaded shaft in a first direction moves the first side component and second side component toward each other and moves the first end plate away from each the axis.

14. The implant of claim 13, wherein the first side component and second side component move parallel to the axis, and wherein the first end plate moves perpendicular to the axis.

15. The implant of claim 13, wherein the first end plate is spaced apart from the axis at a dimension greater in an expanded position than in an unexpanded position.

16. The implant of claim 13, wherein movement of the first side component and second side component pivot the first hinge component relative to the first end plate.

17. The implant of claim 13, wherein the first hinge component is perpendicular to the axis when the first end plate is in an expanded position.

18. The implant of claim 13, wherein a second movement of the expansion/contraction member moves the first side component and second side component away from each other and moves the first end plate toward the axis.

* * * * *